United States Patent
Lubisch et al.

(10) Patent No.: US 6,346,622 B1
(45) Date of Patent: Feb. 12, 2002

(54) 2-SUBSTITUTED 1,2-BENZISOTHIAZOLE DERIVATIVES AND THEIR USE AS SEROTONIN ANTAGONISTS (5-HT$_{1A}$, 5HT$_{1B}$ AND 5-HT$_{1D}$)

(75) Inventors: Wilfried Lubisch, Mannheim; Uta Dullweber, Frankenthal; Dorothea Starck, Ludwigshafen; Gerd Steiner, Kirchheim; Alfred Bach, Heidelberg; Franz Emling, Ludwigshafen; Xavier Garcia-Ladona, Kandel; Hans-Jürgen Teschendorf, Dudenhofen; Karsten Wicke, Altrip, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/529,828

(22) PCT Filed: Oct. 5, 1998

(86) PCT No.: PCT/EP98/06300

§ 371 Date: Apr. 20, 2000

§ 102(e) Date: Apr. 20, 2000

(87) PCT Pub. No.: WO99/20616

PCT Pub. Date: Apr. 29, 1999

(30) Foreign Application Priority Data

Oct. 22, 1997 (DE) .......................... 197 46 612

(51) Int. Cl.$^7$ ................ A61K 31/425; C07D 403/00; C07D 275/02; C07D 513/00
(52) U.S. Cl. ............ 544/368; 548/214; 548/206; 514/373
(58) Field of Search ............... 540/484, 596; 544/368; 548/206, 214; 514/211.15, 217.03, 373

(56) References Cited

U.S. PATENT DOCUMENTS 4,892,879 A  1/1990  Sorg ............... 514/338
5,130,313 A  7/1992  Comte et al. ...... 514/253

FOREIGN PATENT DOCUMENTS

DE  3620643  * 1/1987
EP  749 967    12/1996

OTHER PUBLICATIONS

Magid Abou–Gharbia et al. J.Med.Chem. Polycy.Aryl & Het . . . as 5HT1A Rec . . . 31, 1382–92, Nov. 1988.*
J.Mokrosz et al..J.Med.Chem. Structure Activ. Relat . . . of Central..,35,2369–74, Nov. 1988.*
J.Med.Chem.,1992,35,2369–2374,Mokrosz et al.
J.Med.Chem.,1988,31, 1382–1392,Abou–Gharbia et al.

* cited by examiner

*Primary Examiner*—Bruck Kifle
*Assistant Examiner*—Suhmaker Patel
(74) *Attorney, Agent, or Firm*—Keil & Weinkauf

(57) ABSTRACT

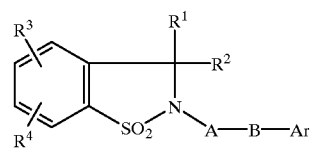

where the substituents have the meanings indicated in the description, their preparation and use as serotonin antagonists.

7 Claims, No Drawings

2-SUBSTITUTED 1,2-BENZISOTHIAZOLE DERIVATIVES AND THEIR USE AS SEROTONIN ANTAGONISTS (5-HT$_{1A}$, 5HT$_{1B}$ AND 5-HT$_{1D}$)

The invention relates to 2-substituted 1,2-benzoisothiazole derivatives, their preparation and use for preparing active ingredients of drugs.

Classical antidepressants, and the newer selective serotonin reuptake inhibitors (SSRIs) exert their antidepressant effect inter alia by inhibiting active reuptake of the transmitter into the presynaptic nerve endings. Unfortunately, in this case the antidepressant effect has its onset only after treatment for at least 3 weeks, moreover, about 30% of patients are therapy-resistant.

Blockade of presynaptic serotonin autoreceptors increases, by abolishing negative coupling, the serotonin release and thus the instantaneous transmitter concentration in the synaptic cleft. This increase in the transmitter concentration is regarded as the principle of the antidepressant effect. This mechanism of action differs from that of previously disclosed antidepressants which activate both the presynaptic and somatodendritic autoreceptors and therefore result in a delayed onset of action only after desensitization of these autoreceptors. Direct autoreceptor blockade bypasses this effect.

It is known that although the thiazole derivatives described in DE 3620643 have affinity for 5-HT$_{1A}$ receptors they have no 5-HT$_{1B}$ affinity.

According to current knowledge, the presynaptic serotonin autoreceptor is of the 5-HT$_{1B}$ subtype (Fink et al., Arch. Pharmacol. 352 (1995), 451). Selective blockade thereof by 5-HT$_{1B/D}$ antagonists increases serotonin release in the brain: G. W. Price et al., Behavioural Brain Research 73 (1996), 79–82; P. H. Hutson et al., Neuropharmacology Vol. 34, No. 4 (1995), 383–392.

However, surprisingly, the selective 5-HT$_{1B}$ antagonist GR 127 935 reduces serotonin release in the cortex after systemic administration. One explanation might be stimulation of somatodendritic 5-HT$_{1A}$ receptors in the raphe region by the released serotonin, which inhibits the rate of firing of serotonergic neurones and thus serotonin excretion (M. Skingle et al., Neuropharmacology Vol. 34, No. 4 (1995), 377–382, 393–402).

One strategy for bypassing the autoinhibitory effects in serotonergic areas of origin thus aims at blockade of the presynaptic 5-HT1B [sic] receptors. This hypothesis is supported by the observation that the effect of paroxetine on serotonin release in the dorsal raphe nucleus of the rat is potentiated by the 5-HT$_{1B}$ receptor antagonist GR 127 935 (Davidson and Stamford, Neuroscience Letts., 188 (1995), 41).

The second strategy includes blockade of both types of autoreceptors, namely the 5-HT$_{1A}$ receptors, in order to enhance neuronal firing, and the 5-HT$_{1B}$ receptors, in order to increase terminal serotonin release (Starkey and Skingle, Neuropharmacology 33 (3–4) (1994),393).

5-HT$_{1B/D}$ antagonists, alone or coupled to a 5-HT$_{1A}$ receptor antagonist component, ought therefore to cause a greater increase in serotonin release in the brain and might therefore entail advantages in the therapy of depression and related psychological disorders.

It has now been found that 2-substituted 1,2-benzoisothiazole derivatives of the formula I

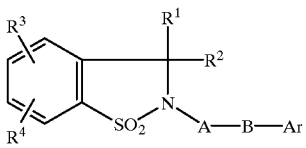

I where
R$^1$ and R$^2$ are, independently of one another (C$_{1-6}$) alkyl,
R$^3$ and R$^4$ are, independently of one another, hydrogen, (C$_{1-6}$) alkyl branched or unbranched, OH, O—(C$_{1-6}$)-alkyl branched or unbranched, F, Cl, Br, I, trifluoromethyl, NR$^5$R$^6$, CO$_2$R$^7$, nitro, cyano, pyrrole, a phenylalkyl C$_1$–C$_4$ radical which in turn can be substituted on the aromatic system by F, Cl, Br, I, C$_1$–C$_4$ alkyl, C$_1$–C$_4$ alkoxy, trifluoromethyl, hydroxyl, amino, cyano or nitro,
R$^5$ and R$^6$ are, independently of one another, hydrogen, (C$_{1-6}$) alkyl branched or unbranched, COPh, CO$_2$tBu, CO—(C$_{1-4}$)-alkyl or together are a 5- or 6-membered ring which may contain a second nitrogen (e.g. piperazine),
R$^7$ is hydrogen and (C$_{1-6}$) alkyl branched or unbranched,
A is branched or unbranched (C$_{1-10}$)-alkylene or straight-chain or branched (C$_{2-10}$)-alkylene, which comprises at least one group Z which is selected from O, S, NR$^7$, cyclopropyl, CHOH, a double or a triple bond,
B is 4-piperidine, 4-tetrahydro-1,2,3,6-pyridine, 4-piperazine and the corresponding cyclic compounds enlarged by one methylene group, the linkage to A taking place by one nitrogen atom of B, and
Ar is phenyl which is unsubstituted or substituted by (C$_{1-6}$) alkyl branched or unbranched, O—(C$_{1-6}$)-alkyl branched or unbranched, OH, F, Cl, Br, I, trifluoromethyl, NR$^5$R$^6$, CO$_2$R$^7$, cyano or phenyl or is tetralin, indan, fused aromatic systems such as naphthalene which is unsubstituted or substituted by (C$_{1-4}$) alkyl or O(C$_{1-4}$) alkyl, or anthracene or 5- or 6-membered aromatic heterocycles having 1 or 2 heteroatoms which are selected, independently of one another, from O and N and which may also be fused to other aromatic radicals, for example quinoline, isoquinoline, phthalazine, indole and quinazoline, which in turn may be substituted by phenyl,
and their salts with physiologically tolerated acids, have valuable pharmacological properties.

Preferred compounds of the formula I are those where
R$^1$ and R$^2$ is [sic], independently of one another, methyl or ethyl,
R$^3$ and R$^4$ are, independently of one another, hydrogen, O—(C$_{1-4}$)-alkyl branched or unbranched, F, Cl, Br, trifluoromethyl, NR$^5$R$^6$, nitro, cyano and phenyl,
R$^5$ and R$^6$ are, independently of one another, hydrogen, COPh, CO$_2$tBu, (C$_{1-6}$) alkyl branched or unbranched and CO—(C$_{1-4}$)-alkyl,
A is branched or unbranched (C$_{2-5}$) alkylene or straight-chain or branched (C$_{2-5}$) alkylene, which comprises a group Z which is selected from CHOH, cyclopropyl, a double or a triple bond,
B is 4-piperidine, 4-tetrahydro-1,2,3,6-pyridine, 4-piperazine or homopiperazine, the linkage to A taking place by one nitrogen atom of B, and
Ar is phenyl which is unsubstituted or substituted by (C$_{1-6}$) alkyl branched or unbranched, O—(C$_{1-6}$)-alkyl branched or unbranched, F, Cl, Br, I, trifluoromethyl, $NR^5R^6$, $CO_2R^7$, cyano and phenyl, or tetralin, indan, fused aromatic systems such as naphthalene which is unsubstituted or substituted by $(C_{1-4})$ alkyl or $O(C_{1-4})$ alkyl, or anthracene and 5- or 6-membered aromatic heterocycles having 1 or 2 heteroatoms which are selected, independently of one another, from O and N, and which may be fused to other aromatic radicals.

Particularly preferred compounds of the formula I are the compounds listed in claim 3.

The compounds of the formula I may have one or more centers of asymmetry. The invention therefore includes not only the racemates but also the relevant enantiomers and diastereomers. The invention also includes the respective tautomeric forms.

The novel compounds of the formula I can be prepared by reacting a compound of the formula II

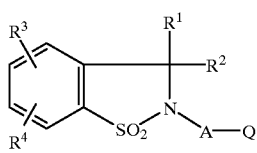

where $R^1$ to $R^4$ and A have the meanings stated above, and Q is a group which can be eliminated (e.g. Cl, Br, I, alkanesulfonyloxy or arylsulfonyloxy), with a secondary amine of the formula III,

where B and Ar have the meanings stated above, in a manner known per se, and converting the compound obtained in this way where appropriate into the addition salt with a physiologically tolerated acid. It is likewise possible to react a compound of the formula IV

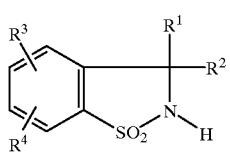

with a compound of the formula V

Q—A—B—Ar   (V)

in a manner known per se. Another synthetic variant is linkage of a compound of the formula VI

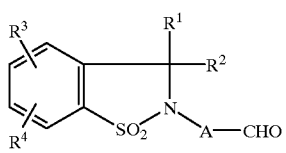

to a compound of the formula III by a reductive amination known per se.

Compounds of the formula III can be synthesized by
1. linking compounds of the formula VII

where $B^1$ is piperazine or homopiperazine and W is hydrogen or one of the usual amino protective groups (e.g. Boc or Cbz), with a compound of the formula VIII

where P is $B(OH)_2$, $SnR_3$, OTf, Br, Cl, or I and R is $C_1$–$C_4$-alkyl, in a known manner; or 2. linking compounds of the formula IX

where $B^2$ is 4-tetrahydro-1,2,3,6-pyridine and the corresponding cyclic compounds enlarged by one methylene group, and $P^1$ is Cl, Br, I, $SnR_3$, where R is $C_1$–$C_4$-alkyl, or OTf to a compound of the formula X

where W, P and Ar each have the abovementioned meanings, and the reactions are carried out by known processes as described, for example, in S. L. Buchwald et al. J. Am. Chem. Soc. 1996, 118, 7215
J. F. Hartwig et al. Tetrahedron Lett. 1995, 36, 3604
J. K. Stille et al. Angew. Chem. 1986, 98, 504
S. L. Buchwald et al. Angew. Chem. 1995, 107, 1456 or J. F.
J. F. Hartwig et al. J.Am. Chem. Soc 1996, 118, 7217 or
J. F. Hartwig et al. J.Org. Chem. 1997, 62, 1268
S. L. Buchwald et al. J.Org. Chem. 1997, 62, 1264 and literature cited therein or
S. L. Buchwald et al J.Am. Chem. Soc 1997, 119, 6054
J. K. Stille, Angew. Chem. 1986, 98, 504 or
J. K. Stille et al. J.Org.Chem. 1990, 55, 3014.
M. Pereyre et al. "Tin in Organic Synthesis", Butterworth 1987; or 3. reducing compounds of the formula (XI)

where $B^2$ has the meaning stated above, to compounds of the formula XII

where $B^3$ is piperidines linked in the 1,4 positions and the corresponding cyclic compounds enlarged by one methylene group, or 4. cyclizing compounds of the formula XIII

where W and Q have the meanings described above, with a compound of the formula XIV

where Ar has the abovementioned meaning, to give compounds of the formula XV

The substances of the formulae III and V required as starting materials for synthesizing the novel compounds are known or can be synthesized by known processes (e.g. Organikum Barth Dt. Verl. der Wiss. 1993 or A. R. Katritzky, C. W. Rees (ed.) Comprehensive Heterocyclic Chemistry Pergamon Press) from analogous precursors.

Further reaction of the compounds prepared according to 1. or 4., with subsequent elimination of any protective groups,

H—B—Ar (III)

to give compounds of the formula V takes place by linkage to compounds of the formula XVI

Q—A—Q' (XVI), where Q and Q' are leaving groups, under conditions known per se.

The substances of the formulae II, IV, VI and of the formulae P—Ar, $NH_2$—Ar, W—$B^1$ and W—$B^2$—$P^1$, which are required as starting materials for synthesizing the novel compounds, are known or can be synthesized from analogous precursors by processes described in the literature (e.g. B. Schulze, K. Illgen J. prakt. Chem. 1997, 339, 1 or K. Auer, E. Hungerbühler, R. W. Lang Chimia 1990, 44, 120 or A. Yokoo et al. Bull. Chem. Soc. Jpn. 1956, 29, 631 or L. B örjeson et al. Acta Chem. Chem. [sic] 1991, 45, 621 or Organikum Barth Dt. Verl. der Wiss. 1993 or A. R. Katritzky, C. W. Rees (ed.) Comprehensive Heterocyclic Chemistry Pergamon Press or The Chemistry of Heterocyclic Compounds J. Wiley & Sons Inc. New York and the literature cited in each of these).

The reactions described above generally take place in an inert organic solvent, e.g. dimethylformamide, acetonitrile, dichloromethane, dimethyl sulfoxide, dimethoxyethane, toluene, ethyl acetate, xylene, a ketone such as acetone or methyl ethyl ketone, an alcohol such as ethanol or n-butanol, or a cyclic saturated ether, e.g. tetrahydrofuran or dioxane.

The reactions generally take place at from 20° C. to the boiling point of the solvent and are generally complete within 1 to 20 hours. An acid-binding agent is present if required, such as sodium or potassium carbonate, sodium methoxide, sodium ethoxide, sodium hydride, organometallic compounds (butyllithium, alkylmagnesium compounds), potassium t-butoxide, pyridine or triethylamine.

The reactions take place where appropriate with use of a catalyst such as transition metals and complexes thereof, e.g. Pd—C, $Pd(PPh_3)_4$, $Pd(OAc)_2$, $Pd(P(oTol)_3)_4$, $Pd_2(dba)_3$ or $Ni(COD)_2$.

The crude product is isolated in a conventional way, for example by filtration, removal of the solvent by distillation or extraction from the reaction mixture.

The novel compounds of the formula I can be purified either by recrystallization from conventional organic solvents or by column chromatography.

The invention includes not only the free 2-substituted 1,2-benzoisothiazole derivatives but also the addition salts of compounds of the formula I with physiologically tolerated acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Further acids which can be used are described in "Forschritte der Arzneimittelforschung", Volume 10, pages 224 et seq., Birkhäuser Verlag, Basel and Stuttgart, 1966.

The acid addition salts are prepared in a conventional way by mixing the free base with the appropriate acid, where appropriate in solution in an organic solvent, for example a lower alcohol such as methanol, ethanol or propanol, an ether such as methyl t-butyl ether, a ketone such as acetone or methyl ethyl ketone or an ester such as ethyl acetate.

The invention accordingly also relates to a therapeutic composition which comprises a compound of the formula I or its pharmacologically acceptable acid addition salt as active ingredient in addition to conventional excipients and diluents, and to the use of the novel compounds for controlling diseases.

The novel compounds can be administered in a conventional way orally or parenterally, intravenously or intramuscularly. The dosage depends on the age, condition and weight of the patient and on the mode of administration. As a rule, the daily dose of active ingredient is about 1–100 mg/kg of body weight on oral administration and 0.1–10 mg/kg of body weight on parenteral administration.

The novel compounds can be used in conventional solid or liquid pharmaceutical forms, e.g. as uncoated or (film-) coated tablets, capsules, powders, granules, suppositories, solutions, ointments, creams or sprays. These are produced in a conventional way. The active ingredients can for this purpose be processed with conventional pharmaceutical auxiliaries such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administraton forms obtained in this way normally contain from 1 to 99% by weight of active ingredient.

The novel compounds have a high affinity for the $5HT_{1B}$, $5-HT_{1D}$ and $5-HT_{1A}$ serotonin receptors. The affinity for these receptors is moreover approximately the same, at least of the same order of magnitude. Furthermore, some of the novel compounds show good serotonin reuptake inhibition, which is a principle implemented in most antidepressants.

These compounds are suitable as drugs for treating pathological states in which the serotonin concentration is reduced and in which it is wished as part of a treatment to block specifically the activity of the $5-HT_{1B}$, $5-HT_{1A}$ and $5-HT_{1D}$ presynaptic receptors without greatly affecting the other receptors at the same time. An example of a pathological state of this type is depression.

The compounds of the present invention may also be beneficial for treating mood disturbances with a central nervous causation, such as seasonal affective disorder and dysthymia. These also include anxiety states such as generalized anxiety, panic attacks, sociophobia, obsessive-compulsive neuroses and post-traumatic stress symptoms, memory disturbances including dementia, amnesias and age-related memory loss, and psychogenic eating disorders such as anorexia nervosa and bulimia nervosa.

The novel compounds may additionally be beneficial for treating endocrine disorders such as hyperprolactinemia and for treating vasospasms (especially of the cerebral vessels), hypertension and gastrointestinal disorders associated with motility and secretion disturbances. Another area of use comprises sexual disorders.

The following examples serve to illustrate the invention without restricting it.

EXAMPLE 1

3,3-Dimethyl-2-[3-(4-(5-tetralinyl)-1-piperazinyl)prop-1-yl]-2,3-dihydro-1,2-benzoisothiazole 1,1-dioxide Preparation of the Starting Materials a) 3,3-Dimethyl-2,3-dihydro-1,2-benzoisothiazole 1,1-dioxide This compound was prepared in a manner known from the literature (K. Auer, E. Hungerbühler, R. W. Lang Chimia 1990, 44, 120). 3,3-Diethyl-2,3-dihydro-1,2-benzoisothiazole 1,1-dioxide (melting point 174° C.) and 3,3-dimethyl-6-nitro-2,3-dihydro-1,2-benzoisothiazole 1,1-dioxide (melting point 187° C.) were obtained in a similar way.

b) 2-(3-Chloroprop-1-yl)-3,3-dimethyl-2,3-dihydro-1,2-benzoisothia-zole 1,1-dioxide A solution of 5.9 g (3 mmol) of 3,3-dimethyl-2,3-dihydro-1,2-benzoisothiazole 1,1-dioxide in 150 ml of DMF at room temperature was, after addition of 3.7 g (3.3 mmol) of potassium t-butoxide, heated under nitrogen to 80° C. Then 14.2 g (9 mmol) of 1-bromo-3-chloropropane were rapidly added and the mixture was stirred at 100° C. for 30 min. Pouring into ice-water was followed by extraction with ether, and the organic phases were washed with water, dried with sodium sulfate and then evaporated so that the product resulted as crystals which could be filtered off with suction. 6.7 g (82%) of substance were obtained. Melting point 107° C.

2-(3-Chloroprop-1-yl)-3,3-diethyl-2,3-dihydro-1,2-benzoisothiazole 1,1-dioxide (melting point 70° C.), 2-(3-chloroprop-1-yl)-3,3-dimethyl-6-nitro-2,3-dihydro-1,2-benzoisothiazole 1,1-dioxide (melting point 146° C.), 2-(2-chloroethyl)-3,3-diethyl-2,3-dihydro-1,2-benzoisothiazole 1,1-dioxide (oil), 2-(2-chloroethyl)-4-chloro-3,3-dimethyl-2,3-dihydro-1,2-benzoisothiazole 1,1-dioxide (oil), 2-(3-chloro-2-methyleneprop-1-yl)-3,3-dimethyl-2,3-dihydro-1,2-benzoisothiazole 1,1-dioxide (melting point 115° C.) and 2-(3-chloropropyl)-3,3-dimethyl-6-nitro-2,3-dihydro-1,2-benzoiso-thiazole 1,1-dioxide (melting point 146° C.) were obtained in a similar way.

c) 1-(5-Tetralinyl)piperazine 14.7 g (0.1 mol) of 5-aminotetralin were refluxed with 18 g (0.11 mol) of bis(β-chloroethyl)amine hydrochloride in 300 ml of n-butanol for 48 h and, after cooling, 5.4 g of sodium carbonate were added and the mixture was refluxed for a further 20 h. The precipitate which formed on cooling was filtered off with suction and taken up in water, and 2N sodium hydroxide solution was added. The aqueous phase was extracted with ethyl acetate, and washing with water and drying over sodium sulfate were followed by evaporation under reduced pressure. It was possible in this way to isolate 10.7 g (50%) of the product as an oil.

4-(1-Piperazinyl)isoquinoline 4.51 g (21.7 mmol) of 4-bromoisoquinoline, 4.65 g (25.0 mmol) of t-butyl piperazine-N-carboxylate, 0.1 g (0.11 mmol) of tris-(dibenzylideneacetone)dipalladium, 0.11 g (0.18 mmol) of 2,2'-bis(diphenylphosphino)-1,1'-binaphthyl and 2.92 g (30.4 mmol) of sodium t-butoxide were mixed in 50 ml of toluene and stirred at 75° C. for 2 h. The reaction mixture was added to ice/sodium chloride and extracted with ethyl acetate, the organic phase was dried over sodium sulfate, and the solvent was removed in a rotary evaporator. The product crystallized out and was filtered off with suction and washed with pentane. 5.5 g (81%) of the Boc-protected piperazine were obtained (melting point 111° C.). 5.2 g (16.6 mmol) of this substance were taken up in 17 ml of dichloromethane and, at 0° C., 17 ml (0.22 mol) of trifluoroacetic acid were slowly added. The mixture was stirred at 0° C. for 4 h, poured into ice-water and extracted with dichloromethane. The aqueous phase was filtered, made alkaline and extracted with dichloromethane. Drying over sodium sulfate and substantial removal of the solvent were followed by dilution with diethyl ether and precipitation of the hydrochloride with ethereal hydrochloric acid. 3.2 g (67%) of the product were obtained. (Melting point 293° C.).

The following compounds were prepared by processes similar to the two described: 1-(1-naphthyl)diazepane (85° C., hydrochloride), 1-(1-naphthylmethyl)piperazine (oil), 4-(1-piperazinyl)indan (oil), 1-(1-naphthyl)piperazine (82° C.), 4-chloro-1-(1-piperazinyl)-phthalazine (205° C., decomposition) and 4-(1-piperazinyl)-quinazoline (320° C., hydrochloride). Other derivatives were commercially available.

Preparation of the Final Product 1.1 g (5.2 mmol) of 1-(5-tetralinyl)piperazine, 1.5 ml of triethylamine and a trace of potassium iodide were added to a solution of 1.64 g (6.0 mmol) of 2-(3-chloroprop-1-yl)-3,3-dimethyl-2,3-dihydro-1,2-benzoisothiazole 1,1-dioxide in 40 ml of DMF. The reaction mixture was stirred at 100° C. for four hours and then poured in ice-water, and the resulting precipitate was filtered off with suction. Purification took place by recrystallization from isopropanol to result in 1 g (43%) of the product (melting point 140° C.).

NMR: $CDCl_3$ δ7.8 (d, 1H), 7.6 (dd, 1H), 7.5 (dd, 1H), 7.4 (d, 1H), 7.1 (dd, 1H), 6.9 (d, 1H), 6.8 (d, 1H), 3.4 (t, 2H), 3.0–2.5 (m, 14H), 2.1 (tt, 2H), 1.8–1.7 (m, 4H), 1.5 (s, 6H) ppm.

The following compounds were obtained in a similar way:

EXAMPLE 2

3,3-Dimethyl-2-[3-(4-(2-phenyl-4-quinazolinyl)-1-piperazinyl)prop-1-yl]-2,3-dihydro-1,2-benzoisothiazole 1,1-dioxide (melting point 269° C., hydrochloride).

EXAMPLE 3

3,3-Dimethyl-2-[3-(4-(2-quinolinyl)-1-piperazinyl)-prop-1-yl]-2,3-dihydro-1,2-benzoisothiazole 1,1-dioxide (melting point 63° C.).

EXAMPLE 4

3,3-Dimethyl-2-[3-(4-(1-naphthyl)-1-diazepanyl)-prop-1-yl]-2,3-dihydro-1,2-benzoisothiazole 1,1-dioxide (melting point 126° C., hydrochloride).

EXAMPLE 5

3,3-Dimethyl-2-[3-(4-(4-chloro-1-phthalazinyl)-1-piperazinyl)-eth-1-yl]-2,3-dihydro-1,2-benzoisothiazole 1,1-dioxide (melting point 190° C.).

EXAMPLE 6

3,3-Dimethyl-2-[3-(4-(1-naphthyl)-1-piperazinyl)-2-methyleneprop-1-yl]-2,3-dihydro-1,2-benzoisothiazole 1,1-dioxide (melting point 193° C.).

EXAMPLE 7

3,3-Dimethyl-2-[2-(4-(4-quinazolinyl)-1-piperazinyl)-eth-1-yl]-2,3-dihydro-1,2-benzoisothiazole 1,1-dioxide (melting point 178° C., hydrochloride).

EXAMPLE 8

3,3-Dimethyl-2-[2-(4-(1-naphthyl)-1-piperazinyl)-eth-1-yl]-2,3-dihydro-1,2-benzoisothiazole 1,1-dioxide (melting point 282° C., hydrochloride).

EXAMPLE 9

3,3-Dimethyl-2-[2-(4-isoquinolin-4-yl)-1-piperazinyl)-eth-1-yl]-2,3-dihydro-1,2-benzoisothiazole 1,1-dioxide (melting point 243° C., hydrochloride).

EXAMPLE 10

3,3-Diethyl-2-[2-(4-(1-naphthyl)-1-piperazinyl)-eth-1-yl]-2,3-di-hydro-1,2-benzoisothiazole 1,1-dioxide (oil).

EXAMPLE 11

3,3-Dimethyl-2-[3-(4-(1-naphthyl)-1-piperazinyl)-prop-1-yl]-6-(1-pyrrolyl)-2,3-dihydro-1,2-benzoisothiazole 1,1-dioxide (melting point 269° C., hydrochloride).

The pyrrole ring was assembled by reacting 3,3-dimethyl-2-[3-(4-(1-naphthyl)-1-piperazinyl)prop-1-yl]-6-amino-2,3-dihydro-1,2-benzoisothiazole 1,1-dioxide with 2,5-dimethoxytetrahydrofuran in glacial acetic acid at 100° C. (1 h) in 86% yield.

EXAMPLE 12
3,3-Dimethyl-2-[3-(4-(1-naphthyl)-1-piperazinyl)-prop-1-yl]-6-benzoylamido-2,3-dihydro-1,2-benzoisothiazole 1,1-dioxide (melting point 127° C.).

EXAMPLE 13
3,3-Dimethyl-2-[3-(4-(1-naphthyl)-1-piperazinyl)-prop-1-yl]-6-nitro-2,3-dihydro-1,2-benzoisothiazole 1,1-dioxide (melting point 203° C.).

EXAMPLE 14
3,3-Dimethyl-2-[2-(4-(2,3-dimethylphenyl)-1-piperazinyl)eth-1-yl]-2,3-dihydro-1,2-benzoisothiazole 1,1-dioxide (melting point 291° C., hydrochloride).

EXAMPLE 15
3,3-Dimethyl-2-[2-(4-(4-indanyl)-1-piperazinyl)-eth-1-yl]-2,3-di-hydro-1,2-benzoisothiazole 1,1-dioxide (melting point 271° C., hydrochloride).

EXAMPLE 16
3,3-Dimethyl-2-[3-(4-(4-chloro-1-naphthyl)-1-piperazinyl)prop-1-yl]-2,3-dihydro-1,2-benzoisothiazole 1,1-dioxide (melting point 151° C.).

EXAMPLE 17
3,3-Dimethyl-2-[3-(4-(2-pyrimidinyl)-1-piperazinyl)-prop-1-yl]-2,3-dihydro-1,2-benzoisothiazole 1,1-dioxide (melting point 263° C., hydrochloride).

EXAMPLE 18
3,3-Dimethyl-2-[2-(4-(4-methoxyphenyl)-1-piperazinyl)eth-1-yl]-2,3-dihydro-1,2-benzoisothiazole 1,1-dioxide (melting point 207° C., hydrochloride).

EXAMPLE 19
3,3-Dimethyl-2-[3-(4-(2-methoxyphenyl)-1-piperazinyl)-2-hydroxy-prop-1-yl]-2,3-dihydro-1,2-benzoisothiazole 1,1-dioxide (melting point 160° C.).

EXAMPLE 20
3,3-Diethyl-2-[3-(4-(1-naphthyl)-1-piperazinyl)-prop-1-yl]-2,3-dihydro-1,2-benzoisothiazole 1,1-dioxide (melting point 179° C.).

EXAMPLE 21
3,3-Dimethyl-2-[3-(4-(2,5-dimethylphenyl)-1-piperazinyl)prop-1-yl]-2,3-dihydro-1,2-benzoisothiazole 1,1-dioxide (melting point 218° C., hydrochloride).

EXAMPLE 22
3,3-Dimethyl-2-[2-(4-(2-cyanophenyl)-1-piperazinyl)eth-1-yl]-2,3-dihydro-1,2-benzoisothiazole 1,1-dioxide (melting point 228° C., hydrochloride).

EXAMPLE 23
3,3-Dimethyl-2-[2-(4-(1-naphthyl)-1-piperazinyl)-eth-1-yl]-4-chloro-2,3-dihydro-1,2-benzoisothiazole 1,1-dioxide.
Preparation of the Starting Materials
a) 4-Chloro-3,3-dimethyl-2,3-dihydro-1,2-benzoisothiazole 1,1-dioxide This compound was prepared as in Example 1a). Yield 7.8 g (70%). (Melting point 121° C.)
b) 2-(2,2-Diethoxyeth-1-yl)-4-chloro-3,3-dimethyl-2,3-dihydro-1,2-benzoisothiazole 1,1-dioxide 7.7 g (33 mmol) of 4-chloro-3,3-dimethyl-2,3-dihydro-1,2-benzoisothiazole 1,1-dioxide, 8.25 ml (55 mmol) of bromoacetaldehyde diethyl acetal and 7.0 g of potassium carbonate were taken up in 100 ml of dry DMF and stirred at 120° C. for 5 h. The reaction mixture was poured into ice-water and then extracted with ethyl acetate, and the organic phase was washed with water and dried over sodium sulfate. The solvent was removed under reduced pressure, the crude product was purified by column chromatography. 7.5 g (65%) of the product were obtained as an oil in this way.
c) 2-(2-Oxoeth-1-yl)-4-chloro-3,3-dimethyl-2,3-dihydro-1,2-benzoisothiazole 1,1-dioxide 7.5 g (21.5 mmol) of 2-(2,2-diethoxyeth-1-yl)-4-chloro-3,3-dimethyl-2,3-dihydro-1,2-benzoisothiazole 1,1-dioxide and 25 ml of concentrated hydrochloric acid were taken up in 25 ml of water and 150 ml of THF and stirred at 40° C. for 1.5 H [sic]. The reaction mixture was neutralized with sodium hydroxide solution and extracted with ether, and the organic phase was dried over sodium sulfate and concentrated under reduced pressure. 5.8 g (98%) of the product were isolated as oil in this way.
Preparation of the Final Product 1.5 g (5.5 mmol) of the aldehyde 24 c), 1.06 g (5 mmol) of naphthylpiperazine (pepared as in Example 1c)) and 0.42 g (7 mmol) of glacial acetic acid in 50 ml of ethanol were stirred at room temperature for 30 min and then 0.5 g (8 mmol) of sodium cyanoborohydride was slowly added. The mixture was stirred at room temperature for 2 h and then poured into an ice/salt mixture and extracted with dichloromethane. Drying with sodium sulfate, removal of the solvent by distillation and subsequent recrystallization from ethanol resulted in 0.9 g (39%) of colorless crystals (melting point 156° C.).

NMR:CDCl$_3$ δ=8.3 (m, 1H), 7.8 (m, 1H), 7.7 (d, 1H), 7.6–7.3 (m, 6H), 7.1 (d, 1H), 3.5 (t, 2H), 3.2 (m, 4H), 3.0–2.8 (m, 6H), 1.8 (s, 6H) ppm.

EXAMPLE 24
Preparation of 3,3-dimethyl-2-[2-(4-(1-naphthyl)tetrahydro-1,2,3,6-pyridin-1-yl)eth-1-yl] 2,3-dihydro-1,2-benzoisothiazole 1,1-dioxide
Synthesis of the Starting Materials
a) N-Boc-4-(Trifluoromethanesulfonyloxy)tetrahydro-1,2,3,6-pyridine A solution of 13.2 g (0.13 mol) of diisopropylamine in 200 ml of THF was deprotonated at −78° C. with 100 ml nBuLi (1.6M in hexane) and, after 30 minutes at this temperature, 20.0 g (0.1 mol) of N-Boc-piperidone dissolved in 50 ml of THF were added dropwise. After a further three hours at −78° C., a solution of 39.3 g (0.11 mol) of N,N,-bistrifluoromethanesulfonylaniline in 50 ml of THF was added, and the mixture was allowed to reach room temperature overnight. For workup, water was added, the mixture was extracted with ether, the organic phases were washed with NaHCO$_3$ solution and water and dried over sodium sulfate, and the solvent was evaporated off. The crude product was purified by flash chromatography (silica gel, mobile phase heptane/ethyl acetate=3/1).

Yield: 20.2 g (60% of theory)

$^1$H-NMR:(270 MHz,CDCl3 [sic]) δ=1.4 (s, 9H); 2.4(m, 2H); 3.6 (t, 2H); 4.1 (m, 2H); 5.8 (m, 1H) ppm.
b) N-Boc-4-(1-Naphthyl)tetrahydro-1,2,3,6-pyridine 22 ml of 2M sodium carbonate solution, 7.63 g (44.4 mmol) of naphthyl-1-boronic acid, 4.13 g (97.6 mmol) of lithium chloride, 0.85 g (4.44 mmol) of copper(I) iodide and 2.1 g (1.77 mmol) of tetrakistriphenylpalladium [sic] were successively added to 14.7 g (44.4 mmol) of the compound described above, dissolved in 115 ml of dimethoxyethane, and the mixture was boiled for 4 h. For workup, aqueous ammonia solution was added and extractive workup was carried out with water and ethyl acetate, and the residue obtained after drying over sodium sulfate and evaporation of the solvent was purified by flash chromatograpy (silica gel, mobile phase heptane/ethyl acetate=4/1).

Yield: 8.2 g (57% of theory)
$^1$H-NMR (270 MHz, CDCl3 [sic]): δ=1.4 (s, 9H); 2.5 (m, 2H); 3.7(t, 2H); 4.1 (m, 2H); 5.8 (m, 1H); 7.2–7.5 (m, 3H); 7.3–8.0 (m, 3H) ppm.

c) 4-(1-Naphthyl)tetrahydro-1,2,3,6-pyridine 7.84 g (25.3 mmol) of N-Boc-4-(1-naphthyl)-3,6-dihydro-2H-pyridine were stirred with 200 ml of ethereal hydrochloric acid at room temperature overnight, and the precipitated product was filtered off and dried.

Yield: 5.5 g (88% of theory).

d) Preparation of the Final Compound 1.0 g (4.1 mmol) of the compound 24c described above was dissolved in 20 ml of methanol and, in the presence of 2.22 g (16.8 mmol) of zinc(II) chloride, firstly 1.27 g (5.3 mmol) of the aldehyde described in Example 23c and then 0.5 g (8.14 mmol) of sodium cyanoborohydride were added. After 16 h at room temperature, workup was carried out as described, and the resulting crude product was purified by chromatography (silica gel, mobile phase dichloromethane/methanol=97/3). A white solid was obtained by precipitating the salt with ethereal hydrochloric acid solution.

Yield: 0.9 g (47% of theory)
$^1$H-NMR (270 MHz, DMSO-d6 [sic]): δ=1.6 (m, 6H);2.6 (m, 1H); 3.1 (m, 1H); 3.4–3.6 (m, 6H); 4.0–4.2 (m, 2H); 5.8 (sbr, 1H); 7.6–8.0 (m, 7H); 8.2 (d, 1H); 12.0 (s, 1H) ppm.

EXAMPLE 25

Preparation of 3,3-dimethyl-2-[2-(4-(1-naphthyl)-1-piperidinyl)eth-1-yl]-2,3-dihydro-1,2-benzoisothiazole 1,1-dioxide a) 4-(1-Naphthyl)piperidine 3.7 g (15.3 mmol) of 4-(1-naphthyl)-1,2,3,6-tetrahydropyridine were dissolved in methanol and hydrogenated, with the addition of 0.8 g of palladium on carbon, with hydrogen at room temperature for 48 h. The catalyst was filtered off, and the solvent was evaporated off.

Yield: 1.8 g (56% of theory)
$^1$H-NMR (270 MHz, CDCl3 [sic]) δ=1.6–1.8 (m, 2H); 2.0 (m, 2H); 2.9 (dt, 2H); 3.3 (d, 2H); 3.5 (tt, 1H); 7.4–7.6 (m, 4H); 7.7 (d, 1H); 7.9 (d, 1H); 8.1 (d, 1H) ppm.

Preparation of the Final Compound 1.5 g (7.1 mmol) of the amine 25a were dissolved in 20 ml of methanol and firstly 3.8 g (28.4 mmol) of zinc chloride and 2.21 g (9.2 mmol) of the aldehyde described in Example 23c, dissolved in 15 ml of methanol, were added, and then 0.89 g (14.2 mmol) of sodium cyanoborohydride was added in portions. After stirring for six hours, insolubles were filtered off, and the mother liquid was concentrated and taken up in ethyl acetate. The organic phase was washed with water and saturated brine, dried over sodium sulfate, filtered and concentrated to afford a yellowish oil.

Yield: 2.2 g (65% of theory)
$^1$H-NMR (270 MHz, CDCl$_3$): δ=1.7–1.9 (m, 8H); 2.0 (m, 2H); 2.7–3.0 (m, 4H); 3.2 (m, 2H); 3.5 (m, 1H); 3.7 (t, 2H); 7.1 (d, 1H); 7.3–7.7 (m, 9H); 8.2 (d, 1H) ppm.

Further preferred novel compounds of the formula I are listed in the following table.

| No | R$^1$/R$^2$ | R$^3$ | R$^4$ | R$^5$ | R$^6$ | R$^7$ | A | B | Ar |
|----|------|----|----|------|------|-----|------|------------|---------------------|
| 26 | Me | H | H | / | / | / | C$_2$ | 4-Piperazine | 2-Me—Ph |
| 27 | Me | H | H | / | / | / | C$_2$ | 4-Piperazine | 2-OH—Ph |
| 28 | Me | H | H | / | / | / | C$_2$ | 4-Piperazine | 2-Br—Ph |
| 29 | Me | H | H | / | / | / | C$_2$ | 4-Piperazine | 2-CF$_3$—Ph |
| 30 | Me | H | H | / | / | / | C$_2$ | 4-Piperazine | 2-OEt—Ph |
| 31 | Me | H | H | Me | Me | / | C$_2$ | 4-Piperazine | 2-NR$^5$R$^6$—Ph |
| 32 | Me | H | H | / | / | / | C$_2$ | 4-Piperazine | 2-O(n-C$_4$)—Ph |
| 33 | Me | H | H | / | / | / | C$_2$ | 4-Piperazine | 2-NO$_2$—Ph |
| 34 | Me | H | H | / | / | / | C$_2$ | 4-Piperazine | 2-F—Ph |
| 35 | Me | H | H | / | / | / | C$_2$ | 4-Piperazine | 2-OMe—Ph |
| 36 | Me | H | H | / | / | / | C$_2$ | 4-Piperazine | 2-CN—Ph |
| 37 | Me | H | H | / | / | / | C$_2$ | 4-Piperazine | 2-Cl—Ph |
| 38 | Me | H | H | / | / | H | C$_2$ | 4-Piperazine | 2-CO$_2$R$^7$—Ph |
| 39 | Me | H | H | / | / | Me | C$_2$ | 4-Piperazine | 2-CO$_2$R$^7$—Ph |
| 40 | Me | H | H | H | H | / | C$_2$ | 4-Piperazine | 2-NR$^5$R$^6$—Ph |
| 41 | Me | H | H | n-C$_3$ | n-C$_3$ | / | C$_2$ | 4-Piperazine | 2-NR$^5$R$^6$—Ph |
| 42 | Me | H | H | i-C$_3$ | i-C$_3$ | / | C$_2$ | 4-Piperazine | 2-NR$^5$R$^6$—Ph |
| 43 | Me | H | H | / | / | / | C$_2$ | 4-Piperazine | 2-I—Ph |
| 44 | Me | H | H | / | / | i-C$_3$ | C$_2$ | 4-Piperazine | 2-CO$_2$R$^7$—Ph |
| 45 | Me | H | H | / | / | / | C$_2$ | 4-Piperazine | Ph |
| 46 | Me | H | H | / | / | / | C$_2$ | 4-Piperazine | 2-Et—Ph |
| 47 | Me | H | H | / | / | / | C$_2$ | 4-Piperazine | 2-iC$_3$—Ph |
| 48 | Me | H | H | / | / | / | C$_2$ | 4-Piperazine | 3-Ph—Ph |
| 49 | Me | H | H | / | / | / | C$_2$ | 4-Piperazine | 3-tBu—Ph |
| 50 | Me | H | H | / | / | / | C$_2$ | 4-Piperazine | 3-Et—Ph |
| 51 | Me | H | H | / | / | Et | C$_2$ | 4-Piperazine | 3-CO$_2$R$^7$—Ph |
| 52 | Me | H | H | / | / | / | C$_2$ | 4-Piperazine | 3-I—Ph |
| 53 | Me | H | H | / | / | / | C$_2$ | 4-Piperazine | 3-Cl—Ph |
| 54 | Me | H | H | / | / | / | C$_2$ | 4-Piperazine | 3-Br—Ph |
| 55 | Me | H | H | / | / | / | C$_2$ | 4-Piperazine | 3-F—Ph |
| 56 | Me | H | H | / | / | / | C$_2$ | 4-Piperazine | 3-CF$_3$—Ph |
| 57 | Me | H | H | H | / | / | C$_2$ | 4-Piperazine | 3-OH—Ph |
| 58 | Me | H | H | / | / | H | C$_2$ | 4-Piperazine | 3-CO$_2$R$^7$—Ph |

-continued

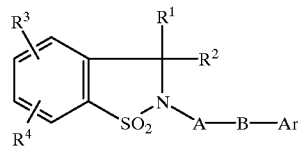

I

| No | R¹/R² | R³ | R⁴ | R⁵ | R⁶ | R⁷ | A | B | Ar |
|---|---|---|---|---|---|---|---|---|---|
| 59 | Me | H | H | H | H | / | $C_2$ | 4-Piperazine | 3-NR⁵R⁶—Ph |
| 60 | Me | H | H | Me | Me | / | $C_2$ | 4-Piperazine | 3-NR⁵R⁶—Ph |
| 61 | Me | H | H | i-$C_3$ | i-$C_3$ | / | $C_2$ | 4-Piperazine | 3-NR⁵R⁶—Ph |
| 62 | Me | H | H | / | / | / | $C_2$ | 4-Piperazine | 3-CN—Ph |
| 63 | Me | H | H | / | / | / | $C_2$ | 4-Piperazine | 3-OMe—Ph |
| 64 | Me | H | H | / | / | / | $C_2$ | 4-Piperazine | 3-NO₂—Ph |
| 65 | Me | H | H | / | / | / | $C_2$ | 4-Piperazine | 3-OEt—Ph |
| 66 | Me | H | H | / | / | / | $C_2$ | 4-Piperazine | 3-O(n-$C_5$)Ph |
| 67 | Me | H | H | / | / | / | $C_2$ | 4-Piperazine | 4-Ph—Ph |
| 68 | Me | H | H | / | / | / | $C_2$ | 4-Piperazine | 4-i$C_3$—Ph |
| 69 | Me | H | H | / | / | / | $C_2$ | 4-Piperazine | 4-n$C_3$—Ph |
| 70 | Me | H | H | / | / | / | $C_2$ | 4-Piperazine | 4-n$C_6$—Ph |
| 71 | Me | H | H | / | / | / | $C_2$ | 4-Piperazine | 4-I—Ph |
| 72 | Me | H | H | / | / | / | $C_2$ | 4-Piperazine | 4-F—Ph |
| 73 | Me | H | H | / | / | / | $C_2$ | 4-Piperazine | 4-Br—Ph |
| 74 | Me | H | H | / | / | / | $C_2$ | 4-Piperazine | 4-Cl—Ph |
| 75 | Me | H | H | / | / | / | $C_2$ | 4-Piperazine | 4-OH—Ph |
| 76 | Me | H | H | / | / | / | $C_2$ | 4-Piperazine | 4-CN—Ph |
| 77 | Me | H | H | / | / | / | $C_2$ | 4-Piperazine | 4-CF₃—Ph |
| 78 | Me | H | H | / | / | / | $C_2$ | 4-Piperazine | 4-NO₂—Ph |
| 79 | Me | H | H | H | H | / | $C_2$ | 4-Piperazine | 4-NR⁵R⁶—Ph |
| 80 | Me | H | H | Me | Me | / | $C_2$ | 4-Piperazine | 4-NR⁵R⁶—Ph |
| 81 | Me | H | H | n-$C_4$ | n-$C_4$ | / | $C_2$ | 4-Piperazine | 4-NR⁵R⁶—Ph |
| 82 | Me | H | H | Me | Et | / | $C_2$ | 4-Piperazine | 4-NR⁵R⁶—Ph |
| 83 | Me | H | H | / | / | H | $C_2$ | 4-Piperazine | 4-CO₂R⁷—Ph |
| 84 | Me | H | H | / | / | Me | $C_2$ | 4-Piperazine | 4-CO₂R⁷—Ph |
| 85 | Me | H | H | / | / | n-$C_5$ | $C_2$ | 4-Piperazine | 4-CO₂R⁷—Ph |
| 86 | Me | H | H | / | / | / | $C_2$ | 4-Piperazine | 4-OMe—Ph |
| 87 | Me | H | H | / | / | / | $C_2$ | 4-Piperazine | 4-OEt—Ph |
| 88 | Me | H | H | / | / | / | $C_2$ | 4-Piperazine | 2-Cl,4-NO₂—Ph |
| 89 | Me | H | H | / | / | / | $C_2$ | 4-Piperazine | 3-Cl,4-Me—Ph |
| 90 | Me | H | H | / | / | / | $C_2$ | 4-Piperazine | 2-CN,6-CN—Ph |
| 91 | Me | H | H | / | / | / | $C_2$ | 4-Piperazine | 2-Me,6-Me—Ph |
| 92 | Me | H | H | / | / | / | $C_2$ | 4-Piperazine | 2-NO₂,4-CF₃—Ph |
| 93 | Me | H | H | / | / | / | $C_2$ | 4-Piperazine | 3-Cl,4-Cl—Ph |
| 94 | Me | H | H | / | / | / | $C_2$ | 4-Piperazine | 2-Me,3-Me—Ph |
| 95 | Me | H | H | / | / | / | $C_2$ | 4-Piperazine | 2-Et,3-Et—Ph |
| 96 | Me | H | H | H | H | / | $C_2$ | 4-Piperazine | 2-NR⁵R⁶,4-Cl—Ph |
| 97 | Me | H | H | H | H | / | $C_2$ | 4-Piperazine | 2-NR⁵R⁶,4-Me—Ph |
| 98 | Me | H | H | Me | Me | / | $C_2$ | 4-Piperazine | 2-NR⁵R⁶,4-Cl—Ph |
| 99 | Me | H | H | / | / | / | $C_2$ | 4-Piperazine | 3-Me,4-Me—Ph |
| 100 | Me | H | H | / | / | / | $C_2$ | 4-Piperazine | 3-Cl,5-Cl—Ph |
| 101 | Me | H | H | / | / | / | $C_2$ | 4-Piperazine | 2-OMe,4-OMe—Ph |
| 102 | Me | H | H | / | / | / | $C_2$ | 4-Piperazine | 3-tBu,5-tBu—Ph |
| 103 | Me | H | H | / | / | / | $C_2$ | 4-Piperazine | 3-tBu,5-CF₃—Ph |
| 104 | Me | H | H | / | / | / | $C_2$ | 4-Piperazine | 2-OMe,5-Cl—Ph |
| 105 | Me | H | H | / | / | / | $C_2$ | 4-Piperazine | 2-OMe,5-OMe—Ph |
| 106 | Me | H | H | / | / | / | $C_2$ | 4-Piperazine | 2-OMe,5-Ph—Ph |
| 107 | Me | H | H | / | / | / | $C_2$ | 4-Piperazine | 2-OMe,4-OMe—Ph |
| 108 | Me | H | H | / | / | / | $C_2$ | 4-Piperazine | 3-CF₃,4-Cl—Ph |
| 109 | Me | H | H | / | / | / | $C_2$ | 4-Piperazine | 2-NO₂,4-CF₃,5-NO₂—Ph |
| 110 | Me | H | H | H | H | / | $C_2$ | 4-Piperazine | 2-NR⁵R⁶,4-Me,5-Cl—Ph |
| 111 | Me | H | H | / | / | / | $C_2$ | 4-Piperazine | 2-OMe,3-Cl,5-Cl—Ph |
| 112 | Me | H | H | / | / | / | $C_2$ | 4-Piperazine | 2-OMe,4-NO₂,5-Me—Ph |
| 113 | Me | H | H | / | / | / | $C_2$ | 4-Piperazine | 2-OMe,4-Cl,5-Me—Ph |
| 114 | Me | H | H | / | / | / | $C_2$ | 4-Piperazine | 2-Me,4-Cl,5-CF₃—Ph |
| 115 | Me | H | H | / | / | / | $C_2$ | 4-Piperazine | 5-Tetralin |
| 116 | Me | H | H | / | / | / | $C_2$ | 4-Piperazine | 4-Indan |
| 117 | Me | H | H | / | / | / | $C_2$ | 4-Piperazine | 1-Tetralin |
| 118 | Me | H | H | / | / | / | $C_2$ | 4-Piperazine | 1-Indan |
| 119 | Me | H | H | / | / | / | $C_2$ | 4-Piperazine | 1-Naphthalene |
| 120 | Me | H | H | / | / | / | $C_2$ | 4-Piperazine | 2-OMe-1-Naphthalene |
| 121 | Me | H | H | / | / | / | $C_2$ | 4-Piperazine | 2-OEt-1-Naphthalene |
| 122 | Me | H | H | / | / | / | $C_2$ | 4-Piperazine | 2-Me-1-Naphthalene |
| 123 | Me | H | H | / | / | / | $C_2$ | 4-Piperazine | 2-Et-1-Naphthalene |
| 124 | Me | H | H | / | / | / | $C_2$ | 4-Piperazine | 8-OMe-1-Naphthalene |
| 125 | Me | H | H | / | / | / | $C_2$ | 4-Piperazine | 8-Me-1-Naphthalene |
| 126 | Me | H | H | / | / | / | $C_2$ | 4-Piperazine | 9-Anthracene |

-continued

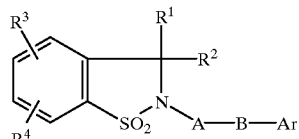

| No | R¹/R² | R³ | R⁴ | R⁵ | R⁶ | R⁷ | A | B | Ar |
|---|---|---|---|---|---|---|---|---|---|
| 127 | Me | H | H | / | / | / | $C_2$ | 4-Piperazine | 3-Indole |
| 128 | Me | H | H | / | / | / | $C_2$ | 4-Piperazine | 2-Quinazoline |
| 129 | Me | H | H | / | / | / | $C_2$ | 4-Piperazine | 4-Quinazoline |
| 130 | Me | H | H | / | / | / | $C_2$ | 4-Piperazine | 2-Quinoxaline |
| 131 | Me | H | H | / | / | / | $C_2$ | 4-Piperazine | 1-Phthalazine |
| 132 | Me | H | H | / | / | / | $C_2$ | 4-Piperazine | 2-Quinoline |
| 133 | Me | H | H | / | / | / | $C_2$ | 4-Piperazine | 3-Quinoline |
| 134 | Me | H | H | / | / | / | $C_2$ | 4-Piperazine | 4-Quinoline |
| 135 | Me | H | H | / | / | / | $C_2$ | 4-Piperazine | 5-Quinoline |
| 136 | Me | H | H | / | / | / | $C_2$ | 4-Piperazine | 1-Isoquinoline |
| 137 | Me | H | H | / | / | / | $C_2$ | 4-Piperazine | 4-Isoquinoline |
| 138 | Me | H | H | / | / | / | $C_2$ | 4-Piperazine | 8-Isoquinoline |
| 139 | Me | H | H | / | / | / | $C_2$ | 4-Piperazine | 7-Benzofuran |
| 140 | Me | H | H | / | / | / | $C_2$ | 4-Piperazine | 3-2H-Chromene |
| 141 | Me | H | H | / | / | / | $C_2$ | 4-Piperazine | 5-Chroman |
| 142 | Me | H | H | / | / | / | $C_2$ | 4-Piperazine | 8-Chroman |
| 143 | Me | H | H | / | / | / | $C_2$ | 4-Piperazine | 2-Pyrimidine |
| 144 | Me | H | H | / | / | / | $C_2$ | 4-Piperazine | 2-tBu,4-$CF_3$-6-Pyrimidine |
| 145 | Me | H | H | / | / | / | $C_2$ | 4-Piperazine | 5-OMe-4-Pyrimidine |
| 146 | Me | H | H | / | / | / | $C_2$ | 4-Piperazine | 4-Pyrimidine |
| 147 | Me | H | H | / | / | / | $C_2$ | 4-Piperazine | 2-Pyrazine |
| 148 | Me | H | H | / | / | / | $C_2$ | 4-Piperazine | 3-Isoxazole |
| 149 | Me | H | H | / | / | / | $C_2$ | 4-Piperazine | 2-Pyridine |
| 150 | Me | H | H | / | / | / | $C_2$ | 4-Piperazine | 3-Pyridine |
| 151 | Me | H | H | / | / | / | $C_2$ | 4-Piperazine | 3-Pyrrole |
| 152 | Me | H | H | / | / | / | $C_2$ | 4-Piperazine | 2-Ph-4-Quinazoline |
| 153 | Me | H | H | / | / | / | $C_2$ | 4-Piperazine | 6-i$C_3$-4-Pyrimidine |
| 154 | Me | H | H | / | / | / | $C_2$ | 4-Piperazine | 7-OMe-1-Naphthalene |
| 155 | Me | H | H | / | / | / | $C_2$ | 4-Piperidine | 2-Me—Ph |
| 156 | Me | H | H | / | / | / | $C_2$ | 4-Piperidine | 2-OH—Ph |
| 157 | Me | H | H | / | / | / | $C_2$ | 4-Piperidine | 2-Br—Ph |
| 158 | Me | H | H | / | / | / | $C_2$ | 4-Piperidine | 2-$CF_3$—Ph |
| 159 | Me | H | H | / | / | / | $C_2$ | 4-Piperidine | 2-OEt—Ph |
| 160 | Me | H | H | Me | Me | / | $C_2$ | 4-Piperidine | 2-$NR^5R^6$—Ph |
| 161 | Me | H | H | / | / | / | $C_2$ | 4-Piperidine | 2-O(n-$C_4$)—Ph |
| 162 | Me | H | H | / | / | / | $C_2$ | 4-Piperidine | 2-$NO_2$—Ph |
| 163 | Me | H | H | / | / | / | $C_2$ | 4-Piperidine | 2-F—Ph |
| 164 | Me | H | H | / | / | / | $C_2$ | 4-Piperidine | 2-OMe—Ph |
| 165 | Me | H | H | / | / | / | $C_2$ | 4-Piperidine | 2-CN—Ph |
| 166 | Me | H | H | / | / | / | $C_2$ | 4-Piperidine | 2-Cl—Ph |
| 167 | Me | H | H | / | / | H | $C_2$ | 4-Piperidine | 2-$CO_2R^7$—Ph |
| 168 | Me | H | H | / | / | Me | $C_2$ | 4-Piperidine | 2-$CO_2R^7$—Ph |
| 169 | Me | H | H | H | H | / | $C_2$ | 4-Piperidine | 2-$NR^5R^6$—Ph |
| 170 | Me | H | H | n-$C_3$ | n-$C_3$ | / | $C_2$ | 4-Piperidine | 2-$NR^5R^6$—Ph |
| 171 | Me | H | H | i-$C_3$ | i-$C_3$ | / | $C_2$ | 4-Piperidine | 2-$NR^5R^6$—Ph |
| 172 | Me | H | H | / | / | / | $C_2$ | 4-Piperidine | 2-I—Ph |
| 173 | Me | H | H | / | / | i-$C_3$ | $C_2$ | 4-Piperidine | 2-$CO_2R^7$—Ph |
| 174 | Me | H | H | / | / | / | $C_2$ | 4-Piperidine | Ph |
| 175 | Me | H | H | / | / | / | $C_2$ | 4-Piperidine | 2-Et—Ph |
| 176 | Me | H | H | / | / | / | $C_2$ | 4-Piperidine | 2-i$C_3$—Ph |
| 177 | Me | H | H | / | / | / | $C_2$ | 4-Piperidine | 3-Ph—Ph |
| 178 | Me | H | H | / | / | / | $C_2$ | 4-Piperidine | 3-tBu—Ph |
| 179 | Me | H | H | / | / | / | $C_2$ | 4-Piperidine | 3-Et—Ph |
| 180 | Me | H | H | / | / | Et | $C_2$ | 4-Piperidine | 3-$CO_2R^7$—Ph |
| 181 | Me | H | H | / | / | / | $C_2$ | 4-Piperidine | 3-I—Ph |
| 182 | Me | H | H | / | / | / | $C_2$ | 4-Piperidine | 3-Cl—Ph |
| 183 | Me | H | H | / | / | / | $C_2$ | 4-Piperidine | 3-Br—Ph |
| 184 | Me | H | H | / | / | / | $C_2$ | 4-Piperidine | 3-F—Ph |
| 185 | Me | H | H | / | / | / | $C_2$ | 4-Piperidine | 3-$CF_3$—Ph |
| 186 | Me | H | H | / | / | / | $C_2$ | 4-Piperidine | 3-OH—Ph |
| 187 | Me | H | H | / | / | H | $C_2$ | 4-Piperidine | 3-$CO_2R^7$—Ph |
| 188 | Me | H | H | H | H | / | $C_2$ | 4-Piperidine | 3-$NR^5R^6$—Ph |
| 189 | Me | H | H | Me | Me | / | $C_2$ | 4-Piperidine | 3-$NR^5R^6$—Ph |
| 190 | Me | H | H | i-$C_3$ | i-$C_3$ | / | $C_2$ | 4-Piperidine | 3-$NR^5R^6$—Ph |
| 191 | Me | H | H | / | / | / | $C_2$ | 4-Piperidine | 3-CN—Ph |
| 192 | Me | H | H | / | / | / | $C_2$ | 4-Piperidine | 3-OMe—Ph |
| 193 | Me | H | H | / | / | / | $C_2$ | 4-Piperidine | 3-$NO_2$—Ph |
| 194 | Me | H | H | / | / | / | $C_2$ | 4-Piperidine | 3-OEt—Ph |

-continued

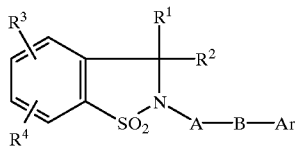

I

| No | R¹/R² | R³ | R⁴ | R⁵ | R⁶ | R⁷ | A | B | Ar |
|---|---|---|---|---|---|---|---|---|---|
| 195 | Me | H | H | / | / | / | $C_2$ | 4-Piperidine | 3-O(n-$C_5$)Ph |
| 196 | Me | H | H | / | / | / | $C_2$ | 4-Piperidine | 4-Ph—Ph |
| 197 | Me | H | H | / | / | / | $C_2$ | 4-Piperidine | 4-i$C_3$—Ph |
| 198 | Me | H | H | / | / | / | $C_2$ | 4-Piperidine | 4-n$C_3$—Ph |
| 199 | Me | H | H | / | / | / | $C_2$ | 4-Piperidine | 4-n$C_6$—Ph |
| 200 | Me | H | H | / | / | / | $C_2$ | 4-Piperidine | 4-I—Ph |
| 201 | Me | H | H | / | / | / | $C_2$ | 4-Piperidine | 4-F—Ph |
| 202 | Me | H | H | / | / | / | $C_2$ | 4-Piperidine | 4-Br—Ph |
| 203 | Me | H | H | / | / | / | $C_2$ | 4-Piperidine | 4-Cl—Ph |
| 204 | Me | H | H | / | / | / | $C_2$ | 4-Piperidine | 4-OH—Ph |
| 205 | Me | H | H | / | / | / | $C_2$ | 4-Piperidine | 4-CN—Ph |
| 206 | Me | H | H | / | / | / | $C_2$ | 4-Piperidine | 4-$CF_3$—Ph |
| 207 | Me | H | H | / | / | / | $C_2$ | 4-Piperidine | 4-$NO_2$—Ph |
| 208 | Me | H | H | / | / | / | $C_2$ | 4-Piperidine | 4-$NR^5R^6$—Ph |
| 209 | Me | H | H | Me | Me | / | $C_2$ | 4-Piperidine | 4-$NR^5R^6$—Ph |
| 210 | Me | H | H | n-$C_4$ | n-$C_4$ | / | $C_2$ | 4-Piperidine | 4-$NR^5R^6$—Ph |
| 211 | Me | H | H | Me | Et | / | $C_2$ | 4-Piperidine | 4-$NR^5R^6$—Ph |
| 212 | Me | H | H | / | / | H | $C_2$ | 4-Piperidine | 4-$CO_2R^7$—Ph |
| 213 | Me | H | H | / | / | Me | $C_2$ | 4-Piperidine | 4-$CO_2R^7$—Ph |
| 214 | Me | H | H | / | / | n-$C_5$ | $C_2$ | 4-Piperidine | 4-$CO_2R^7$—Ph |
| 215 | Me | H | H | / | / | / | $C_2$ | 4-Piperidine | 4-OMe—Ph |
| 216 | Me | H | H | / | / | / | $C_2$ | 4-Piperidine | 4-OEt—Ph |
| 217 | Me | H | H | / | / | / | $C_2$ | 4-Piperidine | 2-Cl,4-$NO_2$—Ph |
| 218 | Me | H | H | / | / | / | $C_2$ | 4-Piperidine | 3-Cl,4-Me—Ph |
| 219 | Me | H | H | / | / | / | $C_2$ | 4-Piperidine | 2-CN,6-CN—Ph |
| 220 | Me | H | H | / | / | / | $C_2$ | 4-Piperidine | 2-Me,6-Me—Ph |
| 221 | Me | H | H | / | / | / | $C_2$ | 4-Piperidine | 2-$NO_2$,4-$CF_3$—Ph |
| 222 | Me | H | H | / | / | / | $C_2$ | 4-Piperidine | 3-Cl,4-Cl—Ph |
| 223 | Me | H | H | / | / | / | $C_2$ | 4-Piperidine | 2-Me,3-Me—Ph |
| 224 | Me | H | H | / | / | / | $C_2$ | 4-Piperidine | 2-Et,3-Et—Ph |
| 225 | Me | H | H | H | H | / | $C_2$ | 4-Piperidine | 2-$NR^5R^6$,4-Cl—Ph |
| 226 | Me | H | H | H | H | / | $C_2$ | 4-Piperidine | 2-$NR^5R^6$,4-Cl—Ph |
| 227 | Me | H | H | Me | Me | / | $C_2$ | 4-Piperidine | 2-$NR^5R^6$,4-Cl—Ph |
| 228 | Me | H | H | / | / | / | $C_2$ | 4-Piperidine | 3-Me,4,Me—Ph |
| 229 | Me | H | H | / | / | / | $C_2$ | 4-Piperidine | 3-Cl,5-Cl—Ph |
| 230 | Me | H | H | / | / | / | $C_2$ | 4-Piperidine | 2-OMe,4-OMe—Ph |
| 231 | Me | H | H | / | / | / | $C_2$ | 4-Piperidine | 3-tBu,5-tBu—Ph |
| 232 | Me | H | H | / | / | / | $C_2$ | 4-Piperidine | 3-tBu,5-$CF_3$—Ph |
| 233 | Me | H | H | / | / | / | $C_2$ | 4-Piperidine | 2-OMe,5-Cl—Ph |
| 234 | Me | H | H | / | / | / | $C_2$ | 4-Piperidine | 2-OMe,5-OMe—Ph |
| 235 | Me | H | H | / | / | / | $C_2$ | 4-Piperidine | 2-OMe,5-Ph—Ph |
| 236 | Me | H | H | / | / | / | $C_2$ | 4-Piperidine | 3-OMe,4-OMe—Ph |
| 237 | Me | H | H | / | / | / | $C_2$ | 4-Piperidine | 3-$CF_3$,4-Cl—Ph |
| 238 | Me | H | H | / | / | / | $C_2$ | 4-Piperidine | 2-$NO_2$,4-$CF_3$,5-$NO_2$—Ph |
| 239 | Me | H | H | H | H | / | $C_2$ | 4-Piperidine | 2-$NR^5R^6$,4-Me,5-Cl—Ph |
| 240 | Me | H | H | / | / | / | $C_2$ | 4-Piperidine | 2-OMe,3-Cl,5-Cl—Ph |
| 241 | Me | H | H | / | / | / | $C_2$ | 4-Piperidine | 2-OMe,4-$NO_2$,5-Me—Ph |
| 242 | Me | H | H | / | / | / | $C_2$ | 4-Piperidine | 2-OMe,4-Cl,5-Me—Ph |
| 243 | Me | H | H | / | / | / | $C_2$ | 4-Piperidine | 2-Me,4-Cl,5-$CF_3$—Ph |
| 244 | Me | H | H | / | / | / | $C_2$ | 4-Piperidine | 5-Tetralin |
| 245 | Me | H | H | / | / | / | $C_2$ | 4-Piperidine | 4-Indan |
| 246 | Me | H | H | / | / | / | $C_2$ | 4-Piperidine | 1-Tetralin |
| 247 | Me | H | H | / | / | / | $C_2$ | 4-Piperidine | 1-Indan |
| 248 | Me | H | H | / | / | / | $C_2$ | 4-Piperidine | 1-Naphthalene |
| 249 | Me | H | H | / | / | / | $C_2$ | 4-Piperidine | 2-OMe-1-Naphthalene |
| 250 | Me | H | H | / | / | / | $C_2$ | 4-Piperidine | 2-OEt-1-Naphthalene |
| 251 | Me | H | H | / | / | / | $C_2$ | 4-Piperidine | 2-Me-1-Naphthalene |
| 252 | Me | H | H | / | / | / | $C_2$ | 4-Piperidine | 2-Et-1-Naphthalene |
| 253 | Me | H | H | / | / | / | $C_2$ | 4-Piperidine | 8-OMe-1-Naphthalene |
| 254 | Me | H | H | / | / | / | $C_2$ | 4-Piperidine | 8-Me-1-Naphthalene |
| 255 | Me | H | H | / | / | / | $C_2$ | 4-Piperidine | 9-Anthracene |
| 256 | Me | H | H | / | / | / | $C_2$ | 4-Piperidine | 3-Indole |
| 257 | Me | H | H | / | / | / | $C_2$ | 4-Piperidine | 2-Quinazoline |
| 258 | Me | H | H | / | / | / | $C_2$ | 4-Piperidine | 4-Quinazoline |
| 259 | Me | H | H | / | / | / | $C_2$ | 4-Piperidine | 2-Quinoxaline |
| 260 | Me | H | H | / | / | ( | $C_2$ | 4-Piperidine | 1-Phthalazine |
| 261 | Me | H | H | / | / | / | $C_2$ | 4-Piperidine | 2-Quinoline |
| 262 | Me | H | H | / | / | / | $C_2$ | 4-Piperidine | 3-Quinoline |

-continued

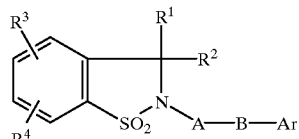

I

| No | R¹/R² | R³ | R⁴ | R⁵ | R⁶ | R⁷ | A | B | Ar |
|---|---|---|---|---|---|---|---|---|---|
| 263 | Me | H | H | / | / | / | $C_2$ | 4-Piperidine | 4-Quinoline |
| 264 | Me | H | H | / | / | / | $C_2$ | 4-Piperidine | 5-Quinoline |
| 265 | Me | H | H | / | / | / | $C_2$ | 4-Piperidine | 1-Isoquinoline |
| 266 | Me | H | H | / | / | / | $C_2$ | 4-Piperidine | 4-Isoquinoline |
| 267 | Me | H | H | / | / | / | $C_2$ | 4-Piperidine | 8-Isoquinoline |
| 268 | Me | H | H | / | / | / | $C_2$ | 4-Piperidine | 7-Benzofuran |
| 269 | Me | H | H | / | / | / | $C_2$ | 4-Piperidine | 3-2H-Chromene |
| 270 | Me | H | H | / | / | / | $C_2$ | 4-Piperidine | 5-Chroman |
| 271 | Me | H | H | / | / | / | $C_2$ | 4-Piperidine | 8-Chroman |
| 272 | Me | H | H | / | / | / | $C_2$ | 4-Piperidine | 2-Pyrimidine |
| 273 | Me | H | H | / | / | / | $C_2$ | 4-Piperidine | 2-tBu,4-$CF_3$-6-Pyrimidine |
| 274 | Me | H | H | / | / | / | $C_2$ | 4-Piperidine | 5-OMe-4-Pyrimidine |
| 275 | Me | H | H | / | / | / | $C_2$ | 4-Piperidine | 4-Pyrimidine |
| 276 | Me | H | H | / | / | / | $C_2$ | 4-Piperidine | 2-Pyrazine |
| 277 | Me | H | H | / | / | / | $C_2$ | 4-Piperidine | 3-Isoxazole |
| 278 | Me | H | H | / | / | / | $C_2$ | 4-Piperidine | 2-Pyridine |
| 279 | Me | H | H | / | / | / | $C_2$ | 4-Piperidine | 3-Pyridine |
| 280 | Me | H | H | / | / | / | $C_2$ | 4-Piperidine | 3-Pyrrole |
| 281 | Me | H | H | / | / | / | $C_2$ | 4-Piperidine | 2-Ph-4-Quinazoline |
| 282 | Me | H | H | / | / | / | $C_2$ | 4-Piperidine | 6-$iC_3$-4-Pyrimidine |
| 283 | Me | H | H | / | / | / | $C_2$ | 4-Piperidine | 7-OMe-1-Naphthalene |
| 284 | Me | H | H | / | / | / | $C_2$ | 4-Tetrahydro-1,2,3,6-pyridine | 2-Me—Ph |
| 285 | Me | H | H | / | / | / | $C_2$ | 4-Tetrahydro-1,2,3,6-pyridine | 2-OH—Ph |
| 286 | Me | H | H | / | / | / | $C_2$ | 4-Tetrahydro-1,2,3,6-pyridine | 2-Br—Ph |
| 287 | Me | H | H | / | / | / | $C_2$ | 4-Tetrahydro-1,2,3,6-pyridine | 2-$CF_3$—Ph |
| 288 | Me | H | H | / | / | / | $C_2$ | 4-Tetrahydro-1,2,3,6-pyridine | 2-OEt—Ph |
| 289 | Me | H | H | H | Me | Me | $C_2$ | 4-Tetrahydro-1,2,3,6-pyridine | 2-$NR^5R^6$—Ph |
| 290 | Me | H | H | / | / | / | $C_2$ | 4-Tetrahydro-1,2,3,6-pyridine | 2-O(n-$C_4$)—Ph |
| 291 | Me | H | H | / | / | / | $C_2$ | 4-Tetrahydro-1,2,3,6-pyridine | 2-$NO_2$—Ph |
| 292 | Me | H | H | / | / | / | $C_2$ | 4-Tetrahydro-1,2,3,6-pyridine | 2-F—Ph |
| 293 | Me | H | H | / | / | / | $C_2$ | 4-Tetrahydro-1,2,3,6-pyridine | 2-OMe—Ph |
| 294 | Me | H | H | / | / | / | $C_2$ | 4-Tetrahydro-1,2,3,6-pyridine | 2-CN—Ph |
| 295 | Me | H | H | / | / | / | $C_2$ | 4-Tetrahydro-1,2,3,6-pyridine | 2-Cl—Ph |
| 296 | Me | H | H | / | / | H | $C_2$ | 4-Tetrahydro-1,2,3,6-pyridine | 2-$CO_2R^7$—Ph |
| 297 | Me | H | H | / | / | Me | $C_2$ | 4-Tetrahydro-1,2,3,6-pyridine | 2-$CO_2R^7$—Ph |
| 298 | Me | H | H | H | H | / | $C_2$ | 4-Tetrahydro-1,2,3,6-pyridine | 2-$NR^5R^6$—Ph |
| 299 | Me | H | H | n-$C_3$ | n-$C_3$ | / | $C_2$ | 4-Tetrahydro-1,2,3,6-pyridine | 2-$NR^5R^6$—Ph |
| 300 | Me | H | H | i-$C_3$ | i-$C_3$ | / | $C_2$ | 4-Tetrahydro-1,2,3,6-pyridine | 2-$NR^5R^6$—Ph |
| 301 | Me | H | H | / | / | / | $C_2$ | 4-Tetrahydro-1,2,3,6-pyridine | 2-I—Ph |
| 302 | Me | H | H | / | / | i-$C_3$ | $C_2$ | 4-Tetrahydro-1,2,3,6-pyridine | 2-$CO_2R^7$—Ph |
| 303 | Me | H | H | / | / | / | $C_2$ | 4-Tetrahydro-1,2,3,6-pyridine | Ph |
| 304 | Me | H | H | / | / | / | $C_2$ | 4-Tetrahydro-1,2,3,6-pyridine | 2-Et—Ph |
| 305 | Me | H | H | / | / | / | $C_2$ | 4-Tetrahydro-1,2,3,6-pyridine | 2-$iC_3$—Ph |
| 306 | Me | H | H | / | / | / | $C_2$ | 4-Tetrahydro-1,2,3,6-pyridine | 3-Ph—Ph |
| 307 | Me | H | H | / | / | / | $C_2$ | 4-Tetrahydro-1,2,3,6-pyridine | 3-tBu—Ph |
| 308 | Me | H | H | / | / | / | $C_2$ | 4-Tetrahydro-1,2,3,6-pyridine | 3-Et—Ph |
| 309 | Me | H | H | / | / | Et | $C_2$ | 4-Tetrahydro-1,2,3,6-pyridine | 3-$CO_2R^7$—Ph |
| 310 | Me | H | H | / | / | / | $C_2$ | 4-Tetrahydro-1,2,3,6-pyridine | 3-I—Ph |
| 311 | Me | H | H | / | / | / | $C_2$ | 4-Tetrahydro-1,2,3,6-pyridine | 3-Cl—Ph |
| 312 | Me | H | H | / | / | / | $C_2$ | 4-Tetrahydro-1,2,3,6-pyridine | 3-Br—Ph |
| 313 | Me | H | H | / | / | / | $C_2$ | 4-Tetrahydro-1,2,3,6-pyridine | 3-F—Ph |
| 314 | Me | H | H | / | / | / | $C_2$ | 4-Tetrahydro-1,2,3,6-pyridine | 3-$CF_3$—Ph |
| 315 | Me | H | H | / | / | / | $C_2$ | 4-Tetrahydro-1,2,3,6-pyridine | 3-OH—Ph |
| 316 | Me | H | H | / | / | H | $C_2$ | 4-Tetrahydro-1,2,3,6-pyridine | 3-$CO_2R^7$—Ph |
| 317 | Me | H | H | H | H | / | $C_2$ | 4-Tetrahydro-1,2,3,6-pyridine | 3-$NR^5R^6$—Ph |
| 318 | Me | H | H | Me | Me | / | $C_2$ | 4-Tetrahydro-1,2,3,6-pyridine | 3-$NR^5R^6$—Ph |
| 319 | Me | H | H | i-$C_3$ | i-$C_3$ | / | $C_2$ | 4-Tetrahydro-1,2,3,6-pyridine | 3-$NR^5R^6$—Ph |
| 320 | Me | H | H | / | / | / | $C_2$ | 4-Tetrahydro-1,2,3,6-pyridine | 3-CN—Ph |
| 321 | Me | H | H | / | / | / | $C_2$ | 4-Tetrahydro-1,2,3,6-pyridine | 3-OMe—Ph |
| 322 | Me | H | H | / | / | / | $C_2$ | 4-Tetrahydro-1,2,3,6-pyridine | 3-$NO_2$—Ph |
| 323 | Me | H | H | / | / | / | $C_2$ | 4-Tetrahydro-1,2,3,6-pyridine | 3-OEt—Ph |
| 324 | Me | H | H | / | / | / | $C_2$ | 4-Tetrahydro-1,2,3,6-pyridine | 3-O(n-$C_5$)Ph |
| 325 | Me | H | H | / | / | / | $C_2$ | 4-Tetrahydro-1,2,3,6-pyridine | 4-Ph—Ph |
| 326 | Me | H | H | / | / | / | $C_2$ | 4-Tetrahydro-1,2,3,6-pyridine | 4-$iC_3$—Ph |
| 327 | Me | H | H | / | / | / | $C_2$ | 4-Tetrahydro-1,2,3,6-pyridine | 4-$nC_3$—Ph |
| 328 | Me | H | H | / | / | / | $C_2$ | 4-Tetrahydro-1,2,3,6-pyridine | 4-$nC_6$—Ph |
| 329 | Me | H | H | / | / | / | $C_2$ | 4-Tetrahydro-1,2,3,6-pyridine | 4-I—Ph |
| 330 | Me | H | H | / | / | / | $C_2$ | 4-Tetrahydro-1,2,3,6-pyridine | 4-F—Ph |

-continued

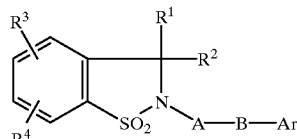

I

| No | R¹/R² | R³ | R⁴ | R⁵ | R⁶ | R⁷ | A | B | Ar |
|---|---|---|---|---|---|---|---|---|---|
| 331 | Me | H | H | / | / | / | $C_2$ | 4-Tetrahydro-1,2,3,6-pyridine | 4-Br—Ph |
| 332 | Me | H | H | / | / | / | $C_2$ | 4-Tetrahydro-1,2,3,6-pyridine | 4-Cl—Ph |
| 333 | Me | H | H | / | / | / | $C_2$ | 4-Tetrahydro-1,2,3,6-pyridine | 4-OH—Ph |
| 334 | Me | H | H | / | / | / | $C_2$ | 4-Tetrahydro-1,2,3,6-pyridine | 4-CN—Ph |
| 335 | Me | H | H | / | / | / | $C_2$ | 4-Tetrahydro-1,2,3,6-pyridine | 4-$CF_3$—Ph |
| 336 | Me | H | H | / | / | / | $C_2$ | 4-Tetrahydro-1,2,3,6-pyridine | 4-$NO_2$—Ph |
| 337 | Me | H | H | H | H | / | $C_2$ | 4-Tetrahydro-1,2,3,6-pyridine | 4-$NR^5R^6$—Ph |
| 338 | Me | H | H | Me | Me | / | $C_2$ | 4-Tetrahydro-1,2,3,6-pyridine | 4-$NR^5R^6$—Ph |
| 339 | Me | H | H | n-$C_4$ | n-$C_4$ | / | $C_2$ | 4-Tetrahydro-1,2,3,6-pyridine | 4-$NR^5R^6$—Ph |
| 340 | Me | H | H | Me | Me | / | $C_2$ | 4-Tetrahydro-1,2,3,6-pyridine | 4-$NR^5R^6$—Ph |
| 341 | Me | H | H | / | / | H | $C_2$ | 4-Tetrahydro-1,2,3,6-pyridine | 4-$CO_2R^7$—Ph |
| 342 | Me | H | H | / | / | Me | $C_2$ | 4-Tetrahydro-1,2,3,6-pyridine | 4-$CO_2R^7$—Ph |
| 343 | Me | H | H | / | / | n-$C_5$ | $C_2$ | 4-Tetrahydro-1,2,3,6-pyridine | 4-$CO_2R^7$—Ph |
| 344 | Me | H | H | / | / | / | $C_2$ | 4-Tetrahydro-1,2,3,6-pyridine | 4-OMe—Ph |
| 345 | Me | H | H | / | / | / | $C_2$ | 4-Tetrahydro-1,2,3,6-pyridine | 4-OEt—Ph |
| 346 | Me | H | H | / | / | / | $C_2$ | 4-Tetrahydro-1,2,3,6-pyridine | 2-Cl,2,3,6-$NO_2$—Ph |
| 347 | Me | H | H | / | / | / | $C_2$ | 4-Tetrahydro-1,2,3,6-pyridine | 3-Cl,2,3,6-Me—Ph |
| 348 | Me | H | H | / | / | / | $C_2$ | 4-Tetrahydro-1,2,3,6-pyridine | 2-CN,6-CN—Ph |
| 349 | Me | H | H | / | / | / | $C_2$ | 4-Tetrahydro-1,2,3,6-pyridine | 2-Me,6-Me—Ph |
| 350 | Me | H | H | / | / | / | $C_2$ | 4-Tetrahydro-1,2,3,6-pyridine | 2-$NO_2$,2,3,6-$CF_3$—Ph |
| 351 | Me | H | H | / | / | / | $C_2$ | 4-Tetrahydro-1,2,3,6-pyridine | 3-Cl,2,3,6-Cl—Ph |
| 352 | Me | H | H | / | / | / | $C_2$ | 4-Tetrahydro-1,2,3,6-pyridine | 2-Me,3-Me—Ph |
| 353 | Me | H | H | / | / | / | $C_2$ | 4-Tetrahydro-1,2,3,6-pyridine | 2-Et,3-Et—Ph |
| 354 | Me | H | H | H | H | / | $C_2$ | 4-Tetrahydro-1,2,3,6-pyridine | 2-$NR^5R^6$,2,3,6-Cl—Ph |
| 355 | Me | H | H | H | H | / | $C_2$ | 4-Tetrahydro-1,2,3,6-pyridine | 2-$NR^5R^6$,2,3,6-Me—Ph |
| 356 | Me | H | H | Me | Me | / | $C_2$ | 4-Tetrahydro-1,2,3,6-pyridine | 2-$NR^5R^6$,2,3,6-Cl—Ph |
| 357 | Me | H | H | / | / | / | $C_2$ | 4-Tetrahydro-1,2,3,6-pyridine | 3-Me,2,3,6-Me—Ph |
| 358 | Me | H | H | / | / | / | $C_2$ | 4-Tetrahydro-1,2,3,6-pyridine | 3-Cl,5-Cl—Ph |
| 359 | Me | H | H | / | / | / | $C_2$ | 4-Tetrahydro-1,2,3,6-pyridine | 2-OMe,2,3,6-OMe—Ph |
| 360 | Me | H | H | / | / | / | $C_2$ | 4-Tetrahydro-1,2,3,6-pyridine | 3-tBu,5-tBu—Ph |
| 361 | Me | H | H | / | / | / | $C_2$ | 4-Tetrahydro-1,2,3,6-pyridine | 3-tBu,5-$CF_3$—Ph |
| 362 | Me | H | H | / | / | / | $C_2$ | 4-Tetrahydro-1,2,3,6-pyridine | 2-OMe,5-Cl—Ph |
| 363 | Me | H | H | / | / | / | $C_2$ | 4-Tetrahydro-1,2,3,6-pyridine | 2-OMe,5-OMe—Ph |
| 364 | Me | H | H | / | / | / | $C_2$ | 4-Tetrahydro-1,2,3,6-pyridine | 2-OMe,5-Ph—Ph |
| 365 | Me | H | H | / | / | / | $C_2$ | 4-Tetrahydro-1,2,3,6-pyridine | 2-OMe,2,3,6-OMe—Ph |
| 366 | Me | H | H | / | / | / | $C_2$ | 4-Tetrahydro-1,2,3,6-pyridine | 3-$CF_3$,2,3,6-Cl—Ph |
| 367 | Me | H | H | / | / | / | $C_2$ | 4-Tetrahydro-1,2,3,6-pyridine | 2-$NO_2$,2,3,6-$CF_3$, 5-$NO_2$—Ph |
| 368 | Me | H | H | H | H | / | $C_2$ | 4-Tetrahydro-1,2,3,6-pyridine | 2-$NR^5R^6$,2,3,6-Me, 5-Cl—Ph |
| 369 | Me | H | H | / | / | / | $C_2$ | 4-Tetrahydro-1,2,3,6-pyridine | 2-OMe,3-Cl,5-Cl—Ph |
| 370 | Me | H | H | / | / | / | $C_2$ | 4-Tetrahydro-1,2,3,6-pyridine | 2-OMe,2,3,6-$NO_2$, 5-Me—Ph |
| 371 | Me | H | H | / | / | / | $C_2$ | 4-Tetrahydro-1,2,3,6-pyridine | 2-OMe,2,3,6-Cl,5-Me—Ph |
| 372 | Me | H | H | / | / | / | $C_2$ | 4-Tetrahydro-1,2,3,6-pyridine | 2-Me,2,3,6-Cl,5-$CF_3$—Ph |
| 373 | Me | H | H | / | / | / | $C_2$ | 4-Tetrahydro-1,2,3,6-pyridine | 4-Tetraline |
| 374 | Me | H | H | / | / | / | $C_2$ | 4-Tetrahydro-1,2,3,6-pyridine | 4-Indan |
| 375 | Me | H | H | / | / | / | $C_2$ | 4-Tetrahydro-1,2,3,6-pyridine | 1-Tetralin |
| 376 | Me | H | H | / | / | / | $C_2$ | 4-Tetrahydro-1,2,3,6-pyridine | 1-Indan |
| 377 | Me | H | H | / | / | / | $C_2$ | 4-Tetrahydro-1,2,3,6-pyridine | 1-Naphthalene |
| 378 | Me | H | H | / | / | / | $C_2$ | 4-Tetrahydro-1,2,3,6-pyridine | 2-OMe-1-Naphthalene |
| 379 | Me | H | H | / | / | / | $C_2$ | 4-Tetrahydro-1,2,3,6-pyridine | 2-OEt-1-Naphthalene |
| 380 | Me | H | H | / | / | / | $C_2$ | 4-Tetrahydro-1,2,3,6-pyridine | 2-Me-1-Naphthalene |
| 381 | Me | H | H | / | / | / | $C_2$ | 4-Tetrahydro-1,2,3,6-pyridine | 2-Et-1-Naphthalene |
| 382 | Me | H | H | / | / | / | $C_2$ | 4-Tetrahydro-1,2,3,6-pyridine | 8-OMe-1-Naphthalene |
| 383 | Me | H | H | / | / | / | $C_2$ | 4-Tetrahydro-1,2,3,6-pyridine | 8-Me-1-Naphthalene |
| 384 | Me | H | H | / | / | / | $C_2$ | 4-Tetrahydro-1,2,3,6-pyridine | 9-Anthracene |
| 385 | Me | H | H | / | / | / | $C_2$ | 4-Tetrahydro-1,2,3,6-pyridine | 3-Indole |
| 386 | Me | H | H | / | / | / | $C_2$ | 4-Tetrahydro-1,2,3,6-pyridine | 2-Quinazoline |
| 387 | Me | H | H | / | / | / | $C_2$ | 4-Tetrahydro-1,2,3,6-pyridine | 4-Quinazoline |
| 388 | Me | H | H | / | / | / | $C_2$ | 4-Tetrahydro-1,2,3,6-pyridine | 2-Quinoxaline |
| 389 | Me | H | H | / | / | / | $C_2$ | 4-Tetrahydro-1,2,3,6-pyridine | 1-Phthalazine |
| 390 | Me | H | H | / | / | / | $C_2$ | 4-Tetrahydro-1,2,3,6-pyridine | 2-Quinoline |
| 391 | Me | H | H | / | / | / | $C_2$ | 4-Tetrahydro-1,2,3,6-pyridine | 3-Quinoline |
| 392 | Me | H | H | / | / | / | $C_2$ | 4-Tetrahydro-1,2,3,6-pyridine | 4-Quinoline |
| 393 | Me | H | H | / | / | / | $C_2$ | 4-Tetrahydro-1,2,3,6-pyridine | 5-Quinoline |
| 394 | Me | H | H | / | / | / | $C_2$ | 4-Tetrahydro-1,2,3,6-pyridine | 1-Isoquinoline |
| 395 | Me | H | H | / | / | / | $C_2$ | 4-Tetrahydro-1,2,3,6-pyridine | 4-Isoquinoline |

-continued

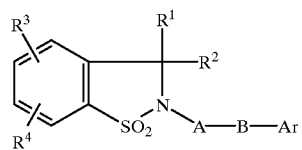

| No | $R^1/R^2$ | $R^3$ | $R^4$ | $R^5$ | $R^6$ | $R^7$ | A | B | Ar |
|---|---|---|---|---|---|---|---|---|---|
| 396 | Me | H | H | / | / | / | $C_2$ | 4-Tetrahydro-1,2,3,6-pyridine | 8-Isoquinoline |
| 397 | Me | H | H | / | / | / | $C_2$ | 4-Tetrahydro-1,2,3,6-pyridine | 7-Benzoferan [sic] |
| 398 | Me | H | H | / | / | / | $C_2$ | 4-Tetrahydro-1,2,3,6-pyridine | 3-2H-Chromene |
| 399 | Me | H | H | / | / | / | $C_2$ | 4-Tetrahydro-1,2,3,6-pyridine | 5-Chroman |
| 400 | Me | H | H | / | / | / | $C_2$ | 4-Tetrahydro-1,2,3,6-pyridine | 8-Chroman |
| 401 | Me | H | H | / | / | / | $C_2$ | 4-Tetrahydro-1,2,3,6-pyridine | 2-Pyrimidine |
| 402 | Me | H | H | / | / | / | $C_2$ | 4-Tetrahydro-1,2,3,6-pyridine | 2-tBu,2,3,6-$CF_3$-6-Pyrimidine |
| 403 | Me | H | H | / | / | / | $C_2$ | 4-Tetrahydro-1,2,3,6-pyridine | 5-OMe-4-Pyrimidine |
| 404 | Me | H | H | / | / | / | $C_2$ | 4-Tetrahydro-1,2,3,6-pyridine | 4-Pyrimidine |
| 405 | Me | H | H | / | / | / | $C_2$ | 4-Tetrahydro-1,2,3,6-pyridine | 2-Pyrazine |
| 406 | Me | H | H | / | / | / | $C_2$ | 4-Tetrahydro-1,2,3,6-pyridine | 3-Isoxazole |
| 407 | Me | H | H | / | / | / | $C_2$ | 4-Tetrahydro-1,2,3,6-pyridine | 2-Pyridine |
| 408 | Me | H | H | / | / | / | $C_2$ | 4-Tetrahydro-1,2,3,6-pyridine | 3-Pyridine |
| 409 | Me | H | H | / | / | / | $C_2$ | 4-Tetrahydro-1,2,3,6-pyridine | 3-Pyrrole |
| 410 | Me | H | H | / | / | / | $C_2$ | 4-Tetrahydro-1,2,3,6-pyridine | 2-Ph-4-Quinazoline |
| 411 | Me | H | H | / | / | / | $C_2$ | 4-Tetrahydro-1,2,3,6-pyridine | 6-$iC_3$-4-Pyrimidine |
| 412 | Me | H | H | / | / | / | $C_2$ | 4-Tetrahydro-1,2,3,6-pyridine | 7-OMe-1-Naphthalene |
| 413 | Me | H | H | / | / | / | $C_2$ | 4-Homopiperazine | 2-Me—Ph |
| 414 | Me | H | H | / | / | / | $C_2$ | 4-Homopiperazine | 2-OH—Ph |
| 415 | Me | H | H | / | / | / | $C_2$ | 4-Homopiperazine | 2-Br—Ph |
| 416 | Me | H | H | / | / | / | $C_2$ | 4-Homopiperazine | 2-$CF_3$—Ph |
| 417 | Me | H | H | / | / | / | $C_2$ | 4-Homopiperazine | 2-OMe—Ph |
| 418 | Me | H | H | / | / | / | $C_2$ | 4-Homopiperazine | 2-CN—Ph |
| 419 | Me | H | H | / | / | / | $C_2$ | 4-Homopiperazine | Ph |
| 420 | Me | H | H | H | H | / | $C_2$ | 4-Homopiperazine | 2-$NR^5R^6$—Ph |
| 421 | Me | H | H | Me | Me | / | $C_2$ | 4-Homopiperazine | 2-$NR^5R^6$—Ph |
| 422 | Me | H | H | / | / | H | $C_2$ | 4-Homopiperazine | 2-$CO_2R^7$—Ph |
| 423 | Me | H | H | / | / | Me | $C_2$ | 4-Homopiperazine | 2-$CO_2R^7$—Ph |
| 424 | Me | H | H | / | / | / | $C_2$ | 4-Homopiperazine | 3-tBu—Ph |
| 425 | Me | H | H | / | / | / | $C_2$ | 4-Homopiperazine | 3-Me—Ph |
| 426 | Me | H | H | / | / | / | $C_2$ | 4-Homopiperazine | 3-$CF_3$—Ph |
| 427 | Me | H | H | / | / | / | $C_2$ | 4-Homopiperazine | 3-Cl—Ph |
| 428 | Me | H | H | / | / | / | $C_2$ | 4-Homopiperazine | 3-OMe—Ph |
| 429 | Me | H | H | / | / | / | $C_2$ | 4-Homopiperazine | 4-$NO_2$—Ph |
| 430 | Me | H | H | / | / | / | $C_2$ | 4-Homopiperazine | 4-Ph—Ph |
| 431 | Me | H | H | / | / | / | $C_2$ | 4-Homopiperazine | 4-F—Ph |
| 432 | Me | H | H | / | / | / | $C_2$ | 4-Homopiperazine | 3-Cl,4-Me Ph |
| 433 | Me | H | H | / | / | / | $C_2$ | 4-Homopiperazine | 2-Me,6-Me Ph |
| 434 | Me | H | H | / | / | / | $C_2$ | 4-Homopiperazine | 2-Me,3-Me Ph |
| 435 | Me | H | H | / | / | / | $C_2$ | 4-Homopiperazine | 2-Et,3,-Et Ph |
| 436 | Me | H | H | / | / | / | $C_2$ | 4-Homopiperazine | 3t-Bu,5-$CF_3$ Ph |
| 437 | Me | H | H | / | / | / | $C_2$ | 4-Homopiperazine | 2-OMe,5-Ph Ph |
| 438 | Me | H | H | / | / | / | $C_2$ | 4-Homopiperazine | 2-OMe,4-Cl,5-Me Ph |
| 439 | Me | H | H | / | / | / | $C_2$ | 4-Homopiperazine | 2-Me,4-Cl,5-$CF_3$ Ph |
| 440 | Me | H | H | / | / | / | $C_2$ | 4-Homopiperazine | 5-Tetralin |
| 441 | Me | H | H | / | / | / | $C_2$ | 4-Homopiperazine | 4-Indan |
| 442 | Me | H | H | / | / | / | $C_2$ | 4-Homopiperazine | 1-Naphthalene |
| 443 | Me | H | H | / | / | / | $C_2$ | 4-Homopiperazine | 2-OMe-1-Naphthalene |
| 444 | Me | H | H | / | / | / | $C_2$ | 4-Homopiperazine | 2-Me-1-Naphthalene |
| 445 | Me | H | H | / | / | / | $C_2$ | 4-Homopiperazine | 7-OMe-1-Naphthalene |
| 446 | Me | H | H | / | / | / | $C_2$ | 4-Homopiperazine | 8-Me-1-Naphthalene |
| 447 | Me | H | H | / | / | / | $C_2$ | 4-Homopiperazine | 2-Quinazoline |
| 448 | Me | H | H | / | / | / | $C_2$ | 4-Homopiperazine | 3-Indole |
| 449 | Me | H | H | / | / | / | $C_2$ | 4-Homopiperazine | 1-Phthalazine |
| 450 | Me | H | H | / | / | / | $C_2$ | 4-Homopiperazine | 2-Quinoline |
| 451 | Me | H | H | / | / | / | $C_2$ | 4-Homopiperazine | 1-Isoquinoline |
| 452 | Me | H | H | / | / | / | $C_2$ | 4-Homopiperazine | 2-Pyrimidine |
| 453 | Me | H | H | / | / | / | $C_2$ | 4-Homopiperazine | 2-tBu,4-$CF_3$-6-Pyrimidine |
| 454 | Me | H | H | / | / | / | $C_2$ | 4-Homopiperazine | 2-Pyridine |
| 455 | Me | H | H | / | / | / | $C_2$ | Azepan | 2-Me—Ph |
| 456 | Me | H | H | / | / | / | $C_2$ | Azepan | Ph |
| 457 | Me | H | H | / | / | / | $C_2$ | Azepan | 2-OMe—Ph |
| 458 | Me | H | H | / | / | / | $C_2$ | Azepan | 2-Cl—Ph |
| 459 | Me | H | H | H | H | / | $C_2$ | Azepan | 2-$NR^5R^6$Ph |
| 460 | Me | H | H | / | / | Me | $C_2$ | Azepan | 2-$CO_2R^7$Ph |
| 461 | Me | H | H | / | / | / | $C_2$ | Azepan | 3-tBu Ph |
| 462 | Me | H | H | / | / | / | $C_2$ | Azepan | 4-Ph—Ph |

-continued

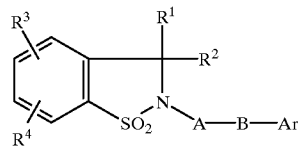

| No | R¹/R² | R³ | R⁴ | R⁵ | R⁶ | R⁷ | A | B | Ar |
|---|---|---|---|---|---|---|---|---|---|
| 463 | Me | H | H | / | / | / | $C_2$ | Azepan | 2-Me,3-Me—Ph |
| 464 | Me | H | H | / | / | / | $C_2$ | Azepan | 2-Me,4-Cl,5-$CF_3$Ph |
| 465 | Me | H | H | / | / | / | $C_2$ | Azepan | 4-Tetraline |
| 466 | Me | H | H | / | / | / | $C_2$ | Azepan | 4-Indan |
| 467 | Me | H | H | / | / | / | $C_2$ | Azepan | 1-Naphthalene |
| 468 | Me | H | H | / | / | / | $C_2$ | Azepan | 2-OMe-1-Naphthalene |
| 469 | Me | H | H | / | / | / | $C_2$ | Azepan | 2-Pyrimidine |
| 470 | Me | H | H | / | / | / | $C_2$ | Azepan | 2-Quinoline |
| 471 | Me | H | H | / | / | / | $C_2$ | Azepan | 1-Phthalazine |
| 472 | Me | H | H | / | / | / | $C_2$ | Azepan | 2-tBu,4-$CF_3$-6-Pyrimidine |
| 473 | Me | H | H | / | / | / | $C_2$ | Azepan | 2-Pyridine |
| 474 | Me | H | H | / | / | / | $C_2$ | Azepan | 4-$NO_2$—Ph |
| 475 | Me | H | H | / | / | / | $C_2$ | Azepan | 2-OH—Ph |
| 476 | Me | H | H | / | / | / | $C_2$ | Tetrahydro-2H-azepine | 2-Me—Ph |
| 477 | Me | H | H | / | / | / | $C_2$ | Tetrahydro-2H-azepine | Ph |
| 478 | Me | H | H | / | / | / | $C_2$ | Tetrahydro-2H-azepine | 2-OMe—Ph |
| 479 | Me | H | H | / | / | / | $C_2$ | Tetrahydro-2H-azepine | 2-Cl—Ph |
| 480 | Me | H | H | H | H | / | $C_2$ | Tetrahydro-2H-azepine | 2-$NR^5R^6$—Ph |
| 481 | Me | H | H | / | / | Me | $C_2$ | Tetrahydro-2H-azepine | 2-$CO_2R^7$—Ph |
| 482 | Me | H | H | / | / | / | $C_2$ | Tetrahydro-2H-azepine | 3-tBu—Ph |
| 483 | Me | H | H | / | / | / | $C_2$ | Tetrahydro-2H-azepine | 4-Ph—Ph |
| 484 | Me | H | H | / | / | / | $C_2$ | Tetrahydro-2H-azepine | 2-Me,3-Me—Ph |
| 485 | Me | H | H | / | / | / | $C_2$ | Tetrahydro-2H-azepine | 2-Me,4-Cl,5-$CF_3$Ph |
| 486 | Me | H | H | / | / | / | $C_2$ | Tetrahydro-2H-azepine | 5-Tetraline |
| 487 | Me | H | H | / | / | / | $C_2$ | Tetrahydro-2H-azepine | 4-Indan |
| 488 | Me | H | H | / | / | / | $C_2$ | Tetrahydro-2H-azepine | 1-Naphthalene |
| 489 | Me | H | H | / | / | / | $C_2$ | Tetrahydro-2H-azepine | 2-OMe-1-Naphthalene |
| 490 | Me | H | H | / | / | / | $C_2$ | Tetrahydro-2H-azepine | 2-Pyrimidine |
| 491 | Me | H | H | / | / | / | $C_2$ | Tetrahydro-2H-azepine | 2-Quinoline |
| 492 | Me | H | H | / | / | / | $C_2$ | Tetrahydro-2H-azepine | 1-Phthalazine |
| 493 | Me | H | H | / | / | / | $C_2$ | Tetrahydro-2H-azepine | 2-tBu,4-$CF_3$-6-Pyrimidine |
| 494 | Me | H | H | / | / | / | $C_2$ | Tetrahydro-2H-azepine | 2-Pyridine |
| 495 | Me | H | H | / | / | / | $C_2$ | Tetrahydro-2H-azepine | 4-$NO_2$—Ph |
| 496 | Me | H | H | / | / | / | $C_2$ | Tetrahydro-2H-azepine | 2-OH—Ph |
| 497 | Me | H | H | / | / | / | $C_3$ | Piperazine | 2-Me—Ph |
| 498 | Me | H | H | / | / | / | $C_3$ | Piperazine | 2-OMe—Ph |
| 499 | Me | H | H | H | H | / | $C_3$ | Piperazine | 2-$NR^5R^6$—Ph |
| 500 | Me | H | H | / | / | Me | $C_3$ | Piperazine | 2-$CO_2R^7$—Ph |
| 501 | Me | H | H | / | / | / | $C_3$ | Piperazine | 3-tBu—Ph |
| 502 | Me | H | H | / | / | / | $C_3$ | Piperazine | 2-Me,3-Me—Ph |
| 503 | Me | H | H | / | / | / | $C_3$ | Piperazine | 5-Tetraline |
| 504 | Me | H | H | / | / | / | $C_3$ | Piperazine | 4-Indan |
| 505 | Me | H | H | / | / | / | $C_3$ | Piperazine | 1-Naphthalene |
| 506 | Me | H | H | / | / | / | $C_3$ | Piperazine | 2-Me-1-Naphthalene |
| 507 | Me | H | H | / | / | / | $C_3$ | Piperazine | 2-Pyrimidine |
| 508 | Me | H | H | / | / | / | $C_3$ | Piperazine | 1-Phthalazine |
| 509 | Me | H | H | / | / | / | $C_3$ | Piperidine | 2-Me—Ph |
| 510 | Me | H | H | / | / | / | $C_3$ | Piperidine | 2-OMe—Ph |
| 511 | Me | H | H | H | H | / | $C_3$ | Piperidine | 2-$NR^5R^6$—Ph |
| 512 | Me | H | H | / | / | Me | $C_3$ | Piperidine | 2-$CO_2R^7$—Ph |
| 513 | Me | H | H | / | / | / | $C_3$ | Piperidine | 3-tBu—Ph |
| 514 | Me | H | H | / | / | / | $C_3$ | Piperidine | 2-Me,3-Me—Ph |
| 515 | Me | H | H | / | / | / | $C_3$ | Piperidine | 5-Tetraline |
| 516 | Me | H | H | / | / | / | $C_3$ | Piperidine | 4-Indan |
| 517 | Me | H | H | / | / | / | $C_3$ | Piperidine | 1-Naphthalene |
| 518 | Me | H | H | / | / | / | $C_3$ | Piperidine | 2-Me-1-Naphthalene |
| 519 | Me | H | H | / | / | / | $C_3$ | Piperidine | 2-Pyrimidine |
| 520 | Me | H | H | / | / | / | $C_3$ | Piperidine | 1-Phthalazine |
| 521 | Me | H | H | / | / | / | $C_3$ | 4-Tetrahydro-1,2,3,6-pyridine | 2-Me—Ph |
| 522 | Me | H | H | / | / | / | $C_3$ | 4-Tetrahydro-1,2,3,6-pyridine | 2-OMe—Ph |
| 523 | Me | H | H | H | H | / | $C_3$ | 4-Tetrahydro-1,2,3,6-pyridine | 2-$NR^5R^6$—Ph |
| 524 | Me | H | H | / | / | Me | $C_3$ | 4-Tetrahydro-1,2,3,6-pyridine | 2-$CO_2R^7$—Ph |
| 525 | Me | H | H | / | / | / | $C_3$ | 4-Tetrahydro-1,2,3,6-pyridine | 3-tBu—Ph |
| 526 | Me | H | H | / | / | / | $C_3$ | 4-Tetrahydro-1,2,3,6-pyridine | 2-Me,3-Me—Ph |
| 527 | Me | H | H | / | / | / | $C_3$ | 4-Tetrahydro-1,2,3,6-pyridine | 5-Tetraline |
| 528 | Me | H | H | / | / | / | $C_3$ | 4-Tetrahydro-1,2,3,6-pyridine | 4-Indan |
| 529 | Me | H | H | / | / | / | $C_3$ | 4-Tetrahydro-1,2,3,6-pyridine | 1-Naphthalene |
| 530 | Me | H | H | / | / | / | $C_3$ | 4-Tetrahydro-1,2,3,6-pyridine | 2-Me-1-Naphthalene |

-continued

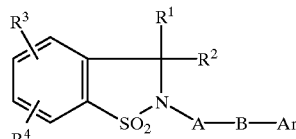

| No | R¹/R² | R³ | R⁴ | R⁵ | R⁶ | R⁷ | A | B | Ar |
|---|---|---|---|---|---|---|---|---|---|
| 531 | Me | H | H | / | / | / | $C_3$ | 4-Tetrahydro-1,2,3,6-pyridine | 2-Pyrimidine |
| 532 | Me | H | H | / | / | / | $C_3$ | 4-Tetrahydro-1,2,3,6-pyridine | 1-Phthalazine |
| 533 | Me | H | H | / | / | / | $C_3$ | Homopiperazine | 2-Me—Ph |
| 534 | Me | H | H | / | / | / | $C_3$ | Homopiperazine | 2-Me,3-Me—Ph |
| 535 | Me | H | H | / | / | / | $C_3$ | Homopiperazine | 5-Tetraline |
| 536 | Me | H | H | / | / | / | $C_3$ | Homopiperazine | 1-Naphthalene |
| 537 | Me | H | H | / | / | / | $C_3$ | Homopiperazine | 2-Me-1-Naphthalene |
| 538 | Me | H | H | / | / | / | $C_3$ | Homopiperazine | 2-Pyrimidine |
| 539 | Me | H | H | / | / | / | $CH_2$—$C(CH_2)$—$CH_2$ | Piperazine | 2-Me—Ph |
| 540 | Me | H | H | / | / | / | $CH_2$—$C(CH_2)$—$CH_2$ | Piperazine | 2-Me,3-Me—Ph |
| 541 | Me | H | H | / | / | / | $CH_2$—$C(CH_2)$—$CH_2$ | Piperazine | 5-Tetraline |
| 542 | Me | H | H | / | / | / | $CH_2$—$C(CH_2)$—$CH_2$ | Piperazine | 1-Naphthalene |
| 543 | Me | H | H | / | / | / | $CH_2$—$C(CH_2)$—$CH_2$ | Piperazine | 2-OMe-1-Naphthalene |
| 544 | Me | H | H | / | / | / | $CH_2$—$C(CH_2)$—$CH_2$ | Piperazine | 2-Pyrimidine |
| 545 | Me | H | H | / | / | / | $CH_2$—$C(CH_2)$—$CH_2$ | Piperazine | 2-Quinoline |
| 546 | Me | H | H | / | / | / | $CH_2$—$C(CH_2)$—$CH_2$ | Piperazine | 2-Me—Ph |
| 547 | Me | H | H | / | / | / | $CH_2$—$C(CH_2)$—$CH_2$ | Piperazine | 2-Me,3-Me—Ph |
| 548 | Me | H | H | / | / | / | $CH_2$—$C(CH_2)$—$CH_2$ | Piperazine | 5-Tetraline |
| 549 | Me | H | H | / | / | / | $CH_2$—$C(CH_2)$—$CH_2$ | Piperazine | 1-Naphthalene |
| 550 | Me | H | H | / | / | / | $CH_2$—$C(CH_2)$—$CH_2$ | Piperazine | 2-OMe-1-Naphthalene |
| 551 | Me | H | H | / | / | / | $CH_2$—$C(CH_2)$—$CH_2$ | Piperazine | 2-Pyrimidine |
| 552 | Me | H | H | / | / | / | $CH_2$—$C(CH_2)$—$CH_2$ | Piperazine | 2-Quinoline |
| 553 | Me | H | H | / | / | / | $CH_2$—$C(CH_2)$—$CH_2$ | Tetrahydropyridine | 2-Me—Ph |
| 554 | Me | H | H | / | / | / | $CH_2$—$C(CH_2)$—$CH_2$ | Tetrahydropyridine | 2-Me,3-Me—Ph |
| 555 | Me | H | H | / | / | / | $CH_2$—$C(CH_2)$—$CH_2$ | Tetrahydropyridine | 5-Tetraline |
| 556 | Me | H | H | / | / | / | $CH_2$—$C(CH_2)$—$CH_2$ | Tetrahydropyridine | 1-Naphthalene |
| 557 | Me | H | H | / | / | / | $CH_2$—$C(CH_2)$—$CH_2$ | Tetrahydropyridine | 2-OMe-1-Naphthalene |
| 558 | Me | H | H | / | / | / | $CH_2$—$C(CH_2)$—$CH_2$ | Tetrahydropyridine | 2-Pyrimidine |
| 559 | Me | H | H | / | / | / | $CH_2$—$C(CH_2)$—$CH_2$ | Tetrahydropyridine | 2-Quinoline |
| 560 | Me | H | H | / | / | / | $CH_2$—$C(CH_2)$—$CH_2$ | Homopiperazine | 2-Me—Ph |
| 561 | Me | H | H | / | / | / | $CH_2$—$C(CH_2)$—$CH_2$ | Homopiperazine | 2-Me,3-Me—Ph |
| 562 | Me | H | H | / | / | / | $CH_2$—$C(CH_2)$—$CH_2$ | Homopiperazine | 5-Tetraline |
| 563 | Me | H | H | / | / | / | $CH_2$—$C(CH_2)$—$CH_2$ | Homopiperazine | 1-Naphthalene |
| 564 | Me | H | H | / | / | / | $CH_2$—$C(CH_2)$—$CH_2$ | Homopiperazine | 2-OMe-1-Naphthalene |
| 565 | Me | H | H | / | / | / | $CH_2$—$C(CH_2)$—$CH_2$ | Homopiperazine | 2-Pyrimidine |
| 566 | Me | H | H | / | / | / | $CH_2$—$C(CH_2)$—$CH_2$ | Homopiperazine | 2-Quinoline |
| 567 | Me | H | H | / | / | / | $CH_2$—$CH(OH)CH_2$ | Piperazine | 2-Me—Ph |
| 568 | Me | H | H | / | / | / | $CH_2$—$CH(OH)CH_2$ | Piperazine | 2-Me,3-Me—Ph |
| 569 | Me | H | H | / | / | / | $CH_2$—$CH(OH)CH_2$ | Piperazine | 5-Tetraline |
| 570 | Me | H | H | / | / | / | $CH_2$—$CH(OH)CH_2$ | Piperazine | 1-Naphthalene |
| 571 | Me | H | H | / | / | / | $CH_2$—$CH(OH)CH_2$ | Piperazine | 2-OMe-1-Naphthalene |
| 572 | Me | H | H | / | / | / | $CH_2$—$CH(OH)CH_2$ | Tetrahydropyridine | 2-Pyrimidine |
| 573 | Me | H | H | / | / | / | $CH_2$—$CH(OH)CH_2$ | Homopiperazine | 2-Quinoline |
| 574 | Me | H | H | / | / | / | $C_2$—N(Me)—$C_2$ | Piperazine | 2-Me—Ph |
| 575 | Me | H | H | / | / | / | $C_2$—N(Me)—$C_2$ | Piperazine | 2-Me,3-Me—Ph |
| 576 | Me | H | H | / | / | / | $C_2$—N(Me)—$C_2$ | Piperazine | 5-Tetraline |
| 577 | Me | H | H | / | / | / | $C_2$—N(Me)—$C_2$ | Piperazine | 1-Naphthalene |
| 578 | Me | H | H | / | / | / | $C_2$—N(Me)—$C_2$ | Piperazine | 2-OMe-1-Naphthalene |
| 579 | Me | H | H | / | / | / | $C_2$—N(Me)—$C_2$ | Tetrahydropyridine | 2-Pyrimidine |
| 580 | Me | H | H | / | / | / | $C_2$—N(Me)—$C_2$ | Homopiperazine | 2-Quinoline |
| 581 | Me | H | H | / | / | / | $CH_2CH(CH_3)$—$CH_2$ | Piperazine | 5-Tetralin |
| 582 | Me | H | H | / | / | / | $CH_2CH(CH_3)$—$CH_2$ | Piperazine | 1-Naphthalene |
| 583 | Me | H | H | / | / | / | $CH_2CH(CH_3)$—$CH_2$ | Piperazine | 2-Me,3-Me—Ph |
| 584 | Me | H | H | / | / | / | $CH_2CH(CH_3)$—$CH_2$ | Tetrahydropyridine | 2-Pyrimidine |
| 585 | Me | H | H | / | / | / | $CH_2CH(CH_3)$—$CH_2$ | Homopiperazine | 2-OMe-Naphthalene |
| 586 | Me | H | H | / | / | / | $C_8$ | Piperazine | 5-Tetralin |
| 587 | Me | H | H | / | / | / | $C_8$ | Piperazine | 1-Naphthalene |
| 588 | Me | H | H | / | / | / | $C_8$ | Piperidine | 2-Me,3-Me—Ph |
| 589 | Me | H | H | / | / | / | $C_8$ | Tetrahydropyridine | 2-Pyrimidine |
| 590 | Me | H | H | / | / | / | $C_8$ | Homopiperazine | 2-OMe-Naphthalene |
| 591 | Me | 5-Me | H | / | / | / | $C_2$ | Piperazine | 5-Tetralin |
| 592 | Me | 5-Me | H | / | / | / | $C_2$ | Piperazine | 1-Naphthalene |
| 593 | Me | 5-Me | H | / | / | / | $C_2$ | Piperazine | 2-OMe—Ph |
| 594 | Me | 5-Me | H | / | / | / | $C_2$ | Piperazine | 2-Pyrimidine |
| 595 | Me | 5-Me | H | / | / | / | $C_2$ | Piperazine | 2-OMe-Naphthalene |
| 596 | Me | 5-Me | H | / | / | / | $C_2$ | Piperidine | 2-Me,3-Me—Ph |
| 597 | Me | 5-Me | H | / | / | / | $C_2$ | Tetrahydropyridine | 2-Quinoline |
| 598 | Me | 5-Me | H | / | / | / | $C_2$ | Homopiperazine | 2-Cl—Ph |

-continued

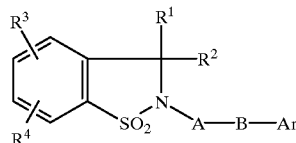

| No | R¹/R² | R³ | R⁴ | R⁵ | R⁶ | R⁷ | A | B | Ar |
|---|---|---|---|---|---|---|---|---|---|
| 599 | Me | 5-Me | H | / | / | / | $C_3$ | Piperazine | 5-Tetralin |
| 600 | Me | 5-Me | H | / | / | / | $C_3$ | Piperazine | 1-Naphthalene |
| 601 | Me | 5-Me | H | / | / | / | $C_3$ | Piperidine | 2-Pyrimidine |
| 602 | Me | 5-Me | H | / | / | / | $C_3$ | Tetrahydropyridine | 2-Me,3Me Ph |
| 603 | Me | 5-Me | H | / | / | / | $C_3$ | Homopiperazine | 2-OMe-Naphthalene |
| 604 | Me | 4-Cl | H | / | / | / | $C_2$ | Piperazine | 1-Naphthalene |
| 605 | Me | 5-OH | H | / | / | / | $C_2$ | Piperazine | 1-Naphthalene |
| 606 | Me | 6-OMe | H | / | / | / | $C_2$ | Piperazine | 1-Naphthalene |
| 607 | Me | 4-F | H | / | / | / | $C_2$ | Piperazine | 1-Naphthalene |
| 608 | Me | 6-OMe | H | / | / | / | $C_2$ | Piperazine | 1-Naphthalene |
| 609 | Me | 4-$CF_3$ | H | / | / | H | $C_2$ | Piperazine | 1-Naphthalene |
| 610 | Me | 6-$CO_2R^7$ | H | / | / | Me | $C_2$ | Piperazine | 1-Naphthalene |
| 611 | Me | 6-$CO_2R^7$ | H | / | / | / | $C_2$ | Piperazine | 1-Naphthalene |
| 612 | Me | 6-$NO_2$ | H | / | / | / | $C_2$ | Piperazine | 1-Naphthalene |
| 613 | Me | 4-CN | H | / | / | / | $C_2$ | Piperazine | 1-Naphthalene |
| 614 | Me | 6-Pyrrol | H | / | / | / | $C_2$ | Piperazine | 1-Naphthalene |
| 615 | Me | 4(-$C_2$—Ph) | H | / | / | / | $C_2$ | Piperazine | 1-Naphthalene |
| 616 | Me | 4[-$C_4$—(4-Cl)Ph] | H | / | / | / | $C_2$ | Piperazine | 1-Naphthalene |
| 617 | Me | 4[-$C_2$—(2-OMe)Ph] | H | / | / | / | $C_2$ | Piperazine | 1-Naphthalene |
| 618 | Me | 4[$C_2$—(3-$CF_2$)Ph] | H | / | / | / | $C_2$ | Piperazine | 1-Naphthalene |
| 619 | Me | 4[$C_2$—(2-Me)Ph] | H | / | / | / | $C_2$ | Piperazine | 1-Naphthalene |
| 620 | Me | 4[$C_2$—(2-$NH_2$)Ph] | H | / | / | / | $C_2$ | Piperazine | 1-Naphthalene |
| 621 | Me | 4[$C_2$—(4-$NO_2$)Ph] | H | / | / | / | $C_2$ | Piperazine | 1-Naphthalene |
| 622 | Me | 4[$C_2$—(4-OH)Ph] | H | / | / | / | $C_2$ | Piperazine | 1-Naphthalene |
| 623 | Me | 6-$NR^5R^6$ | H | Me | H | / | $C_2$ | Piperazine | 1-Naphthalene |
| 624 | Me | 6-$NR^5R^6$ | H | CO Ph | H | / | $C_2$ | Piperazine | 1-Naphthalene |
| 625 | Me | 6-$NR^5R^6$ | H | CO Me | H | / | $C_2$ | Piperazine | 1-Naphthalene |
| 626 | Me | 6-$NR^5R^6$ | H | $CO_2$tBu | H | / | $C_2$ | Piperazine | 1-Naphthalene |
| 627 | Me | 6-$NR^5R^6$ | H | H | H | / | $C_2$ | Piperazine | 1-Naphthalene |
| 628 | Me | 6-$NR^5R^6$ | H | Piperazine | | / | $C_2$ | Piperazine | 1-Naphthalene |
| 629 | Me | 6-$NR^5R^6$ | H | Me | H | / | $C_3$ | Piperazine | 5-Tetralin |
| 630 | Me | 6-$NR^5R^6$ | H | CO Ph | H | / | $C_3$ | Piperazine | 5-Tetralin |
| 631 | Me | 6-$NR^5R^6$ | H | CO Me | H | / | $C_3$ | Piperazine | 5-Tetralin |
| 632 | Me | 6-$NR^5R^6$ | H | / | / | / | $C_3$ | Piperazine | 5-Tetralin |
| 633 | Me | 6-Pyrrol | H | / | / | / | $C_3$ | Piperazine | 5-Tetralin |
| 634 | Me | 6-$NO_2$ | H | / | / | / | $C_3$ | Piperazine | 5-Tetralin |
| 635 | Et | H | H | / | / | / | $C_2$ | Piperazine | 1-Naphthalene |
| 636 | Et | H | H | / | / | / | $C_2$ | Piperazine | 2-OMe—Ph |
| 637 | Et | H | H | / | / | / | $C_2$ | Piperazine | 2-Pyrimidine |
| 638 | Et | H | H | / | / | / | $C_2$ | Piperazine | 2-OMe-1-Naphthalene |
| 639 | Et | H | H | / | / | / | $C_2$ | Piperazine | 2-Me,3-Me—Ph |

We claim:

1. A 2-substituted 1,2-benzoisothiazole derivative of the formula I

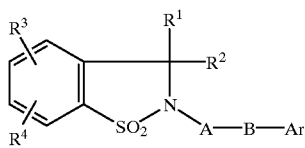

I where
$R^1$ and $R^2$ are, independently of one another, ($C_{1-6}$) alkyl,
$R^3$, $R^4$ are, independently of one another, hydrogen, ($C_{1-6}$) alkyl branched or unbranched, OH, O—($C_{1-6}$)-alkyl branched or unbranched, F, Cl, Br, I, trifluoromethyl, $NR^5R^6$, $CO_2R^7$, nitro, cyano, pyrrole, a phenylalkyl $C_1$–$C_4$ radical which in turn can be substituted on the aromatic system by F, Cl, Br, I, $C_1$–$C_4$ alkyl, $C_1$–$C_4$ alkoxy, trifluoromethyl, hydroxyl, amino, cyano or nitro, $R^5$ and $R^6$ are, independently of one another, hydrogen, ($C_{1-6}$) alkyl branched or unbranched, COPh, $CO_2$tBu, CO—($C_{1-4}$)-alkyl or together are a 5- or 6-membered ring which may contain a second nitrogen, $R^7$ is hydrogen or ($C_{1-6}$) alkyl branched or unbranched, A is branched or unbranched ($C_{1-10}$)-alkylene or straight-chain or branched ($C_{2-10}$)-alkylene which contains one or more groups Z selected from O, S, $NR^7$, cyclopropyl, CHOH, a double or a triple bond, B is 4-piperidine, 4-tetrahydro-1,2,3,6-pyridine, 4-piperazine and homopiperazine, the linkage to A taking place by one nitrogen atom of B, and Ar is phenyl which is unsubstituted or substituted by ($C_{1-6}$) alkyl branched or unbranched, O—($C_{1-6}$)-alkyl branched or unbranched, OH, F, Cl, Br, I, trifluoromethyl, $NR^5R^6$, $CO_2R^7$, cyano or phenyl or is tetralin, indan, a fused aromatic system selected from the group consisting of naphthyl which is unsubstituted or substituted by ($C_{1-4}$) alkyl or O($C_{1-4}$) alkyl, anthracene and 5- or 6-membered aromatic heterocycles having 1 or 2 nitrogen atoms which may be substituted by methyl and/or trifluoromethyl and which may also be fused to other aromatic radicals, its possible enantiomers and diastereomers, tautomeric forms and its salts with physiologically tolerated acids.

2. A 2-substituted 1,2-benzoisothiazole derivative as claimed in claim 1, where $R^1$ and $R^2$ are $(C_{1-2})$ alkyl, $R^3$ and $R^4$ are, independently of one another, hydrogen, O—$(C_{1-4})$-alkyl branched or unbranched, F, Cl, Br, trifluoromethyl, $NR^5R^6$, nitro, cyano and phenyl, $R^5$ and $R^6$ are, independently of one another, hydrogen, COPh, $CO_2tBu$, $(C_{1-6})$ alkyl branched or unbranched and CO—$(C_{1-4})$-alkyl, A is branched or unbranched $(C_{2-5})$ alkylene or straight-chain or branched $(C_{2-5})$ alkylene which contains a group Z which is selected from CHOH, cyclopropyl, a double or a triple bond, B is 4-piperidin-1-yl, 4-tetrahydro-1,2,3,6-pyridin-1-yl, 4-piperazin-1-yl or 4-(1,4-diazepin-1-yl), and Ar is phenyl which is unsubstituted or substituted by $(C_{1-6})$ alkyl branched or unbranched, O—$(C_{1-6})$-alkyl branched or unbranched, F, Cl, trifluoromethyl, $NR^5R^6$, $CO_2R^7$, cyano and phenyl, or tetralin, indan, naphthyl which is unsubstituted or substituted by $(C_{1-4})$ alkyl or O$(C_{1-4})$ alkyl, or 6-membered aromatic heterocycles having 1 or 2 nitrogen atoms and which may also be fused to other aromatic radicals.

3. A 2-substituted 1,2-benzoisothiazole derivative as claimed in claim 1, where $R^1$ and $R^2$ are methyl, $R^3$ and $R^4$ are, independently of one another, hydrogen, nitro, Cl or $NR^5R^6$, $R^5$ and $R^6$ are, independently of one another, hydrogen, COPh and CO—$(C_{1-2})$-alkyl, A is $(C_{2-3})$ alkylene, B is selected from the group consisting of 4-piperidin-1-yl, 4-piperazin-1-yl and 4-tetrahydro-1,2,3,6-pyridin-1-yl, and Ar is phenyl which is unsubstituted or substituted by $(C_{1-2})$ alkyl or O$(C_{1-2})$alkyl in position 2 and 3, or tetralin, indan or naphthalene which is unsubstituted or substituted by $(C_{1-2})$alkyl or O$(C_{1-2})$ alkyl, or pyridine, pyrimidine and isoquinoline.

4. A pharmaceutical composition which is a selective $5HT_{1B}$ and $5HT_{1A}$ antagonist comprising as active ingredient a compound as claimed in claim 1.

5. The 2-substituted 1,2-benzoisothiazole derivative of claim 1, wherein

A is branched or unbranched $(C_{2-5})$-alkylene or straight-chain or branched $(C_{2-5})$-alkylene which contains one or more groups Z selected from cyclopropyl, CHOH and a double or triple bond.

6. A method of treating depression in a subject requiring such treatment which comprises administering an effective amount of the composition of claim 4.

7. A method of treating depression and related disorders in a subject requiring such treatment which comprises administering an effective amount of the composition of claim 4.

* * * * *